(12) United States Patent
Falk et al.

(10) Patent No.: US 10,779,769 B2
(45) Date of Patent: Sep. 22, 2020

(54) METHOD AND SYSTEM FOR EVALUATING A NOISE LEVEL OF A BIOSIGNAL

(71) Applicant: INSTITUT NATIONAL DE LA RECHERCHE SCIENTIFIQUE (INRS), Quebec (CA)

(72) Inventors: Tiago Henrique Falk, Saint-Hubert (CA); Diana Patricia Tobon Vallejo, Montreal (CA); Martin Maier, Verdun (CA)

(73) Assignee: INSTITUT NATIONAL DE LA RECHERCHE SCIENTIFIQUE, Quebec (CA)

( * ) Notice: Subject to any disclaimer, the term of this patent is extended or adjusted under 35 U.S.C. 154(b) by 264 days.

(21) Appl. No.: 15/119,940

(22) PCT Filed: Feb. 17, 2015

(86) PCT No.: PCT/CA2015/000092
§ 371 (c)(1),
(2) Date: Aug. 18, 2016

(87) PCT Pub. No.: WO2015/123753
PCT Pub. Date: Aug. 27, 2015

(65) Prior Publication Data
US 2017/0049400 A1 Feb. 23, 2017

Related U.S. Application Data

(60) Provisional application No. 61/941,842, filed on Feb. 19, 2014.

(51) Int. Cl.
*G01N 33/48* (2006.01)
*G01N 33/50* (2006.01)
(Continued)

(52) U.S. Cl.
CPC .......... *A61B 5/7203* (2013.01); *A61B 5/0024* (2013.01); *A61B 5/0205* (2013.01);
(Continued)

(58) Field of Classification Search
None
See application file for complete search history.

(56) References Cited

U.S. PATENT DOCUMENTS

| 5,956,683 | A | * | 9/1999 | Jacobs | .................... G10L 15/02 704/201 |
|---|---|---|---|---|---|
| 7,496,409 | B2 | | 2/2009 | Greenhut et al. | |

(Continued)

OTHER PUBLICATIONS

International Search Report and Written Opinion for Int. App. No. PCT/CA2015/000092, dated May 7, 2015.
(Continued)

*Primary Examiner* — Russell S Negin
(74) *Attorney, Agent, or Firm* — McDonnell Boehen Hulbert & Berghoff LLP

(57) ABSTRACT

There is described a method for evaluating a level of noise in a biosignal, the method comprising: receiving a time signal representative of a biological activity, the time signal comprising a biological activity component and a noise component; determining a modulation spectrum for the time signal, the modulation spectrum representing a signal frequency as a function of a modulation frequency; from the modulation spectrum determining a first amount of modulation energy corresponding to the biological activity component and a second amount of modulation energy corresponding to the noise component determining an indication of the level of noise using the first and second amounts of modulation energy; and outputting the indication of the level of noise.

16 Claims, 22 Drawing Sheets

(51) Int. Cl.

| | |
|---|---|
| *A61B 5/00* | (2006.01) |
| *A61B 5/0205* | (2006.01) |
| *A61B 5/04* | (2006.01) |
| *A61B 5/0402* | (2006.01) |
| *A61B 5/0476* | (2006.01) |
| *A61B 5/0488* | (2006.01) |
| *A61B 5/0408* | (2006.01) |
| *A61B 5/11* | (2006.01) |
| *A61B 5/0245* | (2006.01) |

(52) U.S. Cl.
CPC ........ *A61B 5/0402* (2013.01); *A61B 5/04014* (2013.01); *A61B 5/04017* (2013.01); *A61B 5/0476* (2013.01); *A61B 5/0488* (2013.01); *A61B 5/6805* (2013.01); *A61B 5/7221* (2013.01); *A61B 5/7257* (2013.01); *A61B 5/0245* (2013.01); *A61B 5/04085* (2013.01); *A61B 5/11* (2013.01)

(56) References Cited

U.S. PATENT DOCUMENTS

| | | |
|---|---|---|
| 2004/0082869 A1 | 4/2004 | Muraki |
| 2007/0069943 A1 | 3/2007 | Adams et al. |
| 2009/0082691 A1 | 3/2009 | Denison et al. |
| 2010/0022903 A1 | 1/2010 | Sitzman et al. |
| 2011/0237904 A1 | 9/2011 | Kim |
| 2011/0254732 A1* | 10/2011 | Martin .................... G01S 19/30 342/357.59 |
| 2013/0053675 A1 | 2/2013 | Kim et al. |
| 2013/0096450 A1 | 4/2013 | Duckert et al. |

OTHER PUBLICATIONS

Falk, T. H., et al., "A Non-Intrusive Quality and Intelligibility Measure of Reverberant and Dereverberated Speech," IEEE Transactions on Audio, Speech, and Language Processing, vol. 18, No. 7, pp. 1766-1774, Sep. 2010.

Falk, T. H., et al., "A Non-Intrusive Quality Measure of Dereverberated Speech," Intl. Workshop for Acoustic Echo and Noise Control, 2008.

Falk, T. H., et al., "Modulation Filtering for Heart and Lung Sound Separation from Breath Sound Recordings," IEEE EMBS Conf., 2008.

Falk, T. H., et al., "Noise Suppression Based on Extending a Speech-Dominated Modulation Band," Intl. Conf. Spoken Lang. Process., 2007.

Falk, T. H., et al., "Non-Intrusive Objective Speech Quality and Intelligibility Prediction for Hearing Instruments in Complex Listening Environments," 2013 IEEE International Conference on Acoustics, Speech and Signal Processing, Vancouver, BC, 2013, pp. 7820-7824.

Falk, T. H., et al., "Spectro-Temporal Analysis of Auscultatory Sounds," New Developments in Biomedical Engineering, Chapter 5, pp. 93-104, Jan. 2010.

Falk, T. H., et al., "Spectro-Temporal Processing for Blind Estimation of Reverberation Time and Single-Ended Quality Measurement of Reverberant Speech," Intl. Conf. Spoken Lang. Process., 2007.

Falk, T. H., et al., "Temporal Dynamics for Blind Measurement of Room Acoustical Parameters," IEEE Transactions on Instrumentation and Measurement, vol. 59, No. 4, pp. 978-989, Apr. 2010.

Santos, J.F., et al., "Towards Blind Reverberation Time Estimation for Non-Speech Signals," Proceedings of Meetings on Acoustics, vol. 19, 2013.

\* cited by examiner

METHOD AND SYSTEM FOR EVALUATING A NOISE LEVEL OF A BIOSIGNAL

CROSS-REFERENCE TO RELATED APPLICATIONS

The present application is a U.S. National Phase Application pursuant to 35 U.S.C. § 371 of International Application No. PCT/CA2015/000092 filed Feb. 17, 2015, which claims priority to U.S. Provisional Patent Application No. 61/941,842, filed Feb. 19, 2014. The entire disclosure contents of these applications are herewith incorporated by reference into the present application.

TECHNICAL FIELD

The present invention relates to the field of methods and systems for analyzing a biosignal, and more particularly for evaluating a noise level of a biosignal.

BACKGROUND

Recent statistics have placed heart disease as the leading cause of death in the United States, representing 1 in every 4 deaths. Worldwide, the statistics are similar and 30% of all global deaths are related to cardiovascular diseases. According to the Heart and Stroke Foundation, the electro-cardiogram (ECG) is an available tool capable of helping clinicians to detect, diagnose, and monitor certain heart diseases. Representative applications can include: detection of abnormal heart rhythms (arrhythmias), ongoing heart attacks, coronary artery blockage, areas of damaged heart muscle from a prior heart attack, enlargement of the heart, inflammation of the sac surrounding the heart (pericarditis), electrolyte imbalances, lung diseases, as well as monitor the effectiveness of certain heart medications or a pacemaker, or even rule out hidden heart diseases in patients about to undergo surgery.

More recently, with the emergence of the so-called "quantified-self" (QS) movement, wireless ECG monitors have proliferated not only within the clinical realm, but also within the sports and consumer markets. A number of devices have reached the market, such as the Hexoskin™ (Carre Technologies™, Canada), nECG™ (Nuubo™, Spain), BioHarness™ (Zephyr™, USA), and Corbelt™ (Corscience™, Germany), to name a few. While such devices have opened doors to emerging telehealth applications, several challenges have been created that still need to be addressed, the most pressing being the quality of the collected ECG signals.

For example, electrocardiograms are known to be susceptible to numerous types of artifacts, such as power line interference, muscle contractions, and baseline drifts due to respiration. Portable wireless systems, in turn, are also sensitive to motion artifacts (as the users are now mobile), electrode contact noise (when sensor loses contact with skin during movement), as well as missing data due to wireless transmission losses. These artifacts can corrupt the ECG signal to a point where the so-called QRS complexes are completely buried in noise, thus limiting the usage of the collected signals for heart rate monitoring or heart disease diagnosis. Such artifacts may be detrimental to automated systems that are aimed at measuring, for example, heart rate variability, a measure commonly used to monitor stress levels and athlete endurance. For this reason, in clinical applications medical personnel often rely on visual inspection of the ECG. With advances in telehealth applications and devices, however, clinicians are now being provided with hours of collected data from numerous modalities. To process such "big data," automated decision support systems are required. In order for reliable systems to be developed, online monitoring of ECG data quality is paramount, such that intelligent signal processing can be used. In fact, a reliable ECG quality index can also be used to train inexperienced staff.

Some ECG quality indices have been developed. Some of the most widely-used measures include: i) ECG root mean square (RMS) value computed within the iso-electric region (i.e., the period between atrial and ventricular depolarization), ii) ratio of the R-peak to noise amplitudes in the isoelectric region, iii) peak-to-RMS ratio, iv) the ratio between in-band (5-40 Hz) and out-of-band spectral power, and v) the kurtosis of the ECG signal. Such measures can be computed for single-lead ECGs, as commonly found in unsupervised telehealth applications, or integrated over multi-lead systems using advanced pattern recognition methods. However, these measures are seldom tested in real-world settings and rely on simulated data. Moreover, measures that rely on peak detection may become unreliable in very noisy scenarios where the peak can be buried in noise. Other more advanced measures have also been reported for multi-lead systems and rely on classifiers, adaptive filtering, or inter-lead features (e.g., lead crossing) to classify ECG signals as acceptable or not. However, these more advanced measures are complex and may present challenges to implement in commercial products.

Therefore, there is a need for an improved method and system for evaluating the quality of a biosignal.

SUMMARY

According to a first broad aspect, there is provided a method for evaluating a level of noise in a biosignal, the method comprising: receiving a time signal representative of a biological activity, the time signal comprising a biological activity component and a noise component; determining a modulation spectrum for the time signal, the modulation spectrum representing a signal frequency as a function of a modulation frequency; from the modulation spectrum determining a first amount of modulation energy corresponding to the biological activity component and a second amount of modulation energy corresponding to the noise component; determining an indication of the level of noise using the first and second amounts of modulation energy; and outputting the indication of the level of noise.

In one embodiment, the step of determining the modulation spectrum comprises: applying a first transform to the time signal, thereby obtaining a time frequency representation of the time signal; and applying a second transform across a time dimension of the time frequency representation, thereby obtaining the modulation spectrum.

In one embodiment, the step of determining the first amount of modulation energy comprises: identifying lobes within the modulation spectrum corresponding to the biological activity component; and calculating the modulation energy corresponding to the lobes.

In one embodiment, the step of determining the second amount of modulation energy comprises calculating an amount of modulation energy contained between the lobes within the modulation spectrum In one embodiment, the step of identifying lobes comprises identifying lobes within at least one of a predefined range of modulation frequency and a predefined range of signal frequency.

In one embodiment, the step of determining an indication comprises calculating a ratio between the first and second amounts of modulation energy, thereby obtaining a quality index indicative of a signal-to-noise ratio.

In one embodiment, the time signal comprises a bio-electrical time signal.

In one embodiment, the bio-electrical time signal comprises an electrocardiogram signal.

In one embodiment, the bio-electrical time signal comprises one of an electromyography signal and an electroencephalography signal.

According to a second broad aspect there is provided a system for evaluating a level of noise in a biosignal, the system comprising: a spectrum generator of receiving a time signal representative of a biological activity and determining a modulation spectrum for the time signal, the modulation spectrum representing a signal frequency as a function of a modulation frequency, the time signal comprising a biological activity component and a noise component; a modulation energy calculating unit for determining from the modulation spectrum a first amount of modulation energy corresponding to the biological activity component and a second amount of modulation energy corresponding to the noise component; and a noise level determining unit for determining an indication of the level of noise using the first and second amounts of modulation energy and outputting the indication of the level of noise.

In one embodiment, the spectrum generator is adapted to: apply a first transform to the time signal in order to obtain a time frequency representation of the time signal; and apply a second transform across a time dimension of the time frequency representation in order to obtain the modulation spectrum.

In one embodiment, in order to obtain the first amount of modulation energy, the modulation energy calculating unit is adapted to: identify lobes within the modulation spectrum corresponding to the bio-electrical activity component; and calculate the modulation energy corresponding to the lobes.

In one embodiment, the modulation energy calculating unit is adapted to calculate an amount of modulation energy contained between the lobes within the modulation spectrum in order to obtain the second amount of modulation energy.

In one embodiment, the modulation energy calculating unit is adapted to identify lobes within at least one of a predefined range of modulation frequency and a predefined range of signal frequency.

In one embodiment, the noise level determining unit is adapted to calculate a ratio between the first and second amounts of modulation energy, thereby obtaining a quality index indicative of the level of noise.

In one embodiment of the system, the time signal comprises a bio-electrical time signal.

In one embodiment of the system, the bio-electrical time signal comprises an electrocardiogram signal.

In one embodiment of the system, the bio-electrical time signal comprises one of an electromyography signal and an electroencephalography signal.

According to another broad aspect, there is provided a computer program product comprising a computer readable memory storing computer executable instructions thereon that when executed by a processing unit perform the method steps of the above method for evaluating a level of noise in a biosignal.

According to a further broad aspect, there is provided a method for filtering noise in a biosignal, the method comprising: receiving a time signal representative of a biological activity, the time signal comprising a biological activity component and a noise component; determining a modulation spectrum for the time signal, the modulation spectrum representing a signal frequency as a function of a modulation frequency; filtering the modulation spectrum in order to remove at least partially the modulation frequencies corresponding to noise; transforming the filtered modulation spectrum into a time domain signal, thereby obtaining a filtered time domain biosignal; and outputting the filtered time domain biosignal.

In one embodiment, the step of determining the modulation spectrum comprises: applying a first transform to the time signal, thereby obtaining a time frequency representation of the time signal; and applying a second transform across a time dimension of the time frequency representation, thereby obtaining the modulation spectrum.

In one embodiment, the modulation spectrum comprises a plurality of lobes corresponding to the biological activity and said filtering the modulation spectrum comprises applying a bandpass filter to the modulation spectrum in order to at least reduce noise components contained in the modulation spectrum.

In one embodiment, the step of applying a bandpass filter comprises applying a time-adaptive bandpass filter to the modulation spectrum.

In one embodiment, the step of filtering the modulation spectrum comprises applying one of a bandstop filter, a highpass filter, and a lowpass filter to the modulation spectrum in order to at least reduce noise components contained in the modulation spectrum.

In one embodiment, the step of transforming the filtered modulation spectrum into a time domain signal comprises: applying a first inverse transform to the filtered modulation spectrum, thereby obtaining a filtered frequency domain representation; and applying a second inverse transform to the filtered frequency domain representation, thereby obtaining the filtered time domain biosignal.

In one embodiment, the time signal comprises a bio-electrical signal.

In one embodiment, the bio-electrical time signal comprises an electrocardiogram signal.

In one embodiment, the bio-electrical time signal comprises one of an electromyography signal and an electroencephalography signal.

According to still another embodiment, there is provided a system for filtering noise in a biosignal, the system comprising: a modulation spectrum generator for receiving a time signal representative of a biological activity and determining a modulation spectrum for the time signal, the modulation spectrum representing a signal frequency as a function of a modulation frequency, the time signal comprising a biological activity component and a noise component; a filtering unit for filtering the modulation spectrum in order to remove at least partially the modulation frequencies corresponding to noise; and a transformation unit for transforming the filtered modulation spectrum into a time domain signal, thereby obtaining a filtered biosignal and outputting the filtered biosignal.

In one embodiment, the modulation spectrum generator is adapted to: apply a first transform to the time signal in order to obtain a time frequency representation of the time signal; and apply a second transform across a time dimension of the time frequency representation in order to obtain the modulation spectrum.

In one embodiment, the modulation spectrum comprises a plurality of lobes corresponding to the biological activity and the filtering unit is adapted to apply a bandpass filter to the modulation spectrum in order to at least reduce a signal component contained between the lobes.

In one embodiment, the modulation spectrum generator is adapted to apply an adaptive bandpass filter to the modulation spectrum.

In one embodiment, the filtering unit is adapted to apply one of a bandstop filter, a highpass filter, and a lowpass filter to the modulation spectrum in order to at least reduce noise components contained in the modulation spectrum.

In one embodiment, the transformation unit is adapted to: apply a first inverse transform to the filtered modulation spectrum in order to obtain a filtered frequency domain representation; and apply a second inverse transform to the filtered frequency domain representation in order to obtain the filtered biosignal.

In one embodiment of the system, the time signal comprises a bio-electrical signal.

In one embodiment of the system, the bio-electrical signal comprises an electrocardiogram signal.

In one embodiment of the system, the bio-electrical signal comprises one of an electromyography signal and an electroencephalography signal.

According to still a further embodiment, there is provided a computer program product comprising a computer readable memory storing computer executable instructions thereon that when executed by a processing unit perform the method steps of the above method for filtering a biosignal.

BRIEF DESCRIPTION OF THE DRAWINGS

Further features and advantages of the present invention will become apparent from the following detailed description, taken in combination with the appended drawings, in which:

FIG. 16a corresponds to the ECG signal of FIG. 15a;

FIG. 16b illustrates an exemplary noisy ECG signal with a signal-to-noise ratio of −10 dB, in accordance with an embodiment;

FIG. 16c illustrates a denoised signal obtained when the method of FIG. 3 is applied to the noisy signal of FIG. 16b, in accordance with an embodiment;

It will be noted that throughout the appended drawings, like features are identified by like reference numerals.

DETAILED DESCRIPTION

As telehealth applications emerge, the need for accurate and reliable biosignal quality indices increases. One typical modality used in remote patient monitoring is the electrocardiogram (ECG), which is inherently susceptible to several different noise sources such as environmental (e.g., powerline interference), experimental (e.g., movement artifacts), and physiological (e.g., muscle and breathing artifacts) noise sources. Accurate measurements of ECG quality can allow for automated decision support systems to make intelligent decisions about patient conditions. This is particularly true for in-home monitoring applications, where the patient is mobile and the ECG signal can be severely corrupted by movement artifacts. In the following, there is described an ECG quality index based on a so-called modulation spectral signal representation. This representation quantifies the rate-of-change of ECG spectral components, which are shown to be different from the rate-of-change of typical ECG noise sources. In one embodiment, the proposed modulation spectral based quality (MS-QI) index can operate with single-lead ECG systems and does not rely on advanced pattern recognition tools. Experiments with synthetic ECG signals corrupted by varying levels of noise and with recorded ECG signals collected during three activity levels (sitting, walking, running) show that the proposed index outperforms two conventional benchmark quality measures, particularly in the scenario involving recorded data in real-world environments. It should be understood that the above-described method and system may be applied to biosignals other than ECGs, such as electromyography signals, electroencephalography signals, and/or the like.

Figure 1:
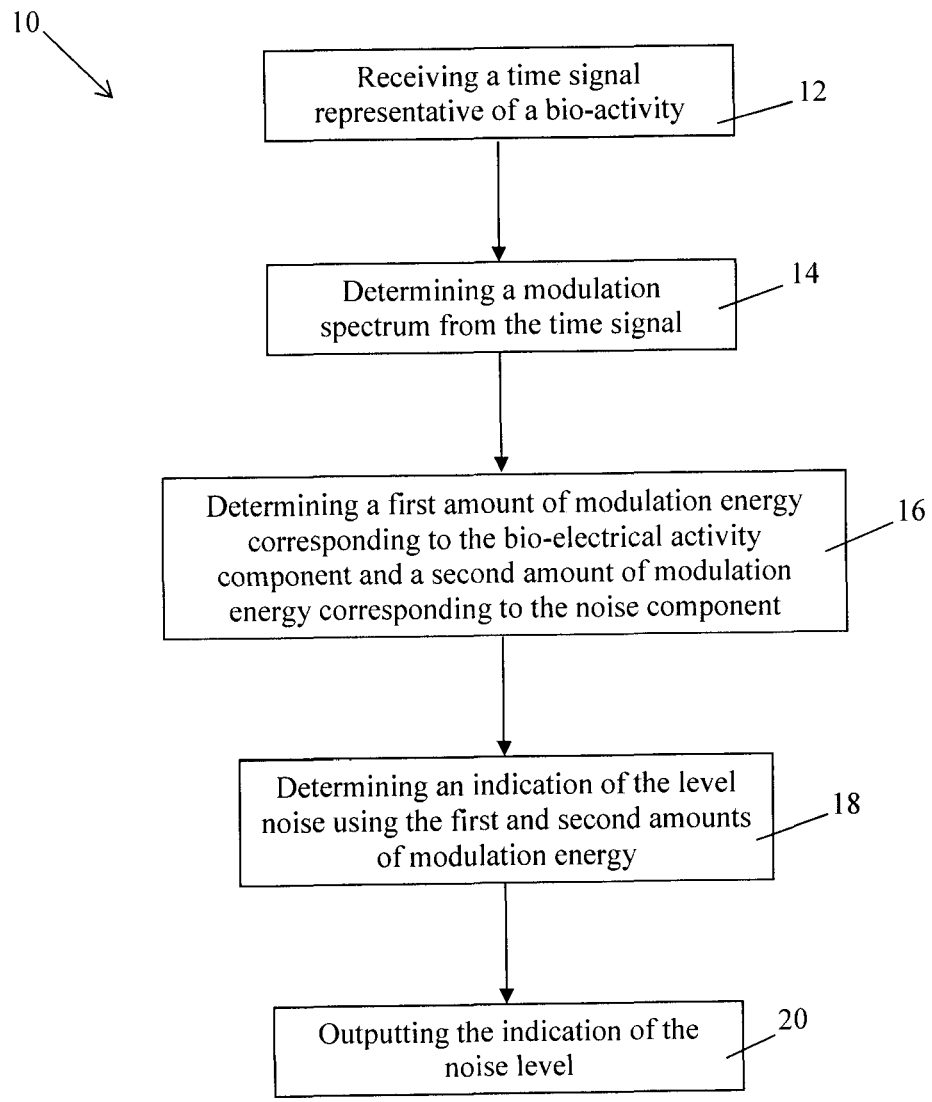
FIG. 1 is a flow chart of a method for evaluating the quality of a biosignal, in accordance with an embodiment.

FIG. 1 illustrates one embodiment of a computer-implemented method 10 for evaluating the quality of a biosignal. The method 10 is performed by at least one processor or processing unit that is connected to a memory and a communication unit for receiving and transmitting data. The first step 12 consists in the processor receiving a measured biosignal, i.e. a time-domain signal of which the amplitude is representative of the amplitude of a biological activity measured by an adequate sensor, via the communication unit. The biosignal may be received from a computing machine such as personal computer, a server, a smartphone, a tablet via a telecommunication network or a wired or wireless connection. In this case, the biosignal is measured by the adequate sensor and then transmitted and stored on the computing machine. The biosignal may also be directly received from the sensor. The time-domain signal may be an electrical signal such as a digital signal or an analog signal. A biological activity may be defined as the driving force causing its corresponding biosignal to change its characteristics. The biosignal may be a bio-electrical signal, or a non-electrical signal. For example, the biosignal may be a bio-electrical signal such as an ECG signal. In this case, the time-domain signal is indicative of the amplitude of a biological activity, i.e. the electrical activity of the heart. Other examples of bio-electrical signals comprise electromyography signals, electroencephalography signals, or the like. In another example, the biosignal may be an acoustic signal of which the amplitude is indicative of the amplitude of a sound of a human body such as breathing, heart sounds, or phonetic and non-phonetic utterances. In a further example, the biosignal may be a mechanical signal such as mechanomyogram (MMG) or a contact accelerometer vibrations signal. In still a further example, the biosignal may be an optical signal such as a signal representing a movement of a being. The time-domain signal comprises two components, i.e. a first component corresponding to the biological activity and a second component corresponding to noise.

At step 14, a modulation spectrum representation of the received biosignal is determined by the processor. It should be understood that the modulation spectrum representation also comprises two components, i.e. a first component corresponding to the biological activity and a second component corresponding to noise since the received biosignal contains a portion that corresponds to the biological activity and another portion that corresponds to noise. The modulation spectrum of a time-domain signal presents the frequency of the signal as a function of the modulation frequency which represents the rate of change of a signal frequency. Therefore, the modulation spectrum provides the modulation frequency, i.e. the rate of change, for each frequency contained in a biosignal.

In one embodiment, two Fourier transforms are successively applied to the time-domain biosignal in order to obtain its modulation spectrum. A first Fourier transform is applied to the time-domain signal in order to obtain a frequency-domain signal. Then, a second and different Fourier transform is applied across the time dimension of the frequency-domain signal to obtain the modulation spectrum, which is a frequency-frequency modulation signal.

While the present description refers to the use of first and second Fourier transforms to convert the time-domain biosignal into a frequency-domain signal and the frequency-domain signal into a frequency-frequency modulation signal, respectively, it should be understood that first and second transforms other than Fourier transforms may be used. Any adequate first transform that may convert the time-domain biosignal into a frequency-domain signal may be used in replacement of the first Fourier transform. Similarly, any adequate second transform that may convert a frequency-domain signal into a frequency-frequency modulation signal may be used in replacement of the second Fourier transform. For example, the first transform may be a Fourier transform while the second transform may be a lapped transform. In one embodiment, the first and/or second transform(s) may be invertible.

Modulation frequencies quantify the rate-of-change of the frequency components of a signal. Since the frequencies associated with the first component, i.e. with the biological activity itself, change at different rates relative to the frequencies associated with the second component, i.e. with the noise coming from artifacts, it is possible in a modulation spectrum to differentiate the modulation frequencies that correspond to the biological activity from the modulation frequencies that correspond to the noise.

Once the modulation spectrum of the biosignal is determined, the next step 16 consists in the processor identifying the component of the modulation spectrum that corresponds to the biological activity, and the other component that corresponds to noise, and calculating the amount of modulation energy for the biological activity and the amount of modulation energy for the noise. In one embodiment, the portion of the modulation spectrum corresponding to the biological activity is first identified, and the remaining of the modulation spectrum is then considered to correspond to noise. Then, the modulation energy for the biological activity is calculated using the identified portion of the modulation spectrum corresponding to the biological activity, and the modulation energy for the noise is calculated using the other portion of the modulation spectrum that corresponds to noise.

While the present description refers to the calculation of the modulation energy of the portions of a modulation spectrum that correspond to the biological activity and noise, it should be understood that the calculation of modulation energies may be replaced by the calculation of modulation intensities or modulation powers. Therefore, calculating a modulation power, a modulation intensity, or a modulation energy are equivalent for the purpose of the present methods and systems.

In an embodiment in which the time-domain biological signal is an ECG signal, the modulation spectrum corresponding to the ECG signal comprises a plurality of frequency lobes substantially regularly spaced apart in modulation frequency, as described below.

The frequency lobes correspond to the modulation frequencies associated with the biological signal, and the remaining of the modulation spectrum, e.g. the portions of the modulation spectrum contained between two adjacent lobes, is associated with the noise contained in the biological signal. The first lobe is first identified by determining the greatest frequency in the modulation spectrum. The modulation frequency having the greatest frequency is identified as being the center modulation frequency fc of the first lobe.

The minimum and maximum modulation frequencies of the first lobe are determined from the center modulation frequency fc using a predefined lobe width W. The minimum modulation frequency of the first lobe is equal to the center modulation frequency minus half of the predefined lobe width, i.e. fc−0.5*W. The maximum modulation frequency of the first lobe is equal to the center modulation frequency plus half of the predefined lobe width, i.e. fc+0.5*W. Each lobe other than the first lobe has a center modulation frequency that is a positive multiple of the central modulation frequency of the first lobe. For example, the second lobe is centered on a modulation frequency that is equal to twice the center modulation frequency of the first lobe, i.e. 2*fc. The minimum and maximum modulation frequencies for the second lobe are obtained by, respectively, subtracting and adding half of the lobe width to the center modulation frequency of the second lobe, i.e. 2*fc−0.5 W and 2*fc+0.5 W, respectively.

Once the lobes have been identified, the modulation energy of the lobes is calculated in order to determine the modulation energy associated with the biological activity, and the modulation energy of the modulation spectrum portions contained between adjacent lobes is calculated to determine the modulation energy associated with noise.

In one embodiment, only the lobes contained within a predetermined range of modulation frequency is considered. For example, only the first five lobes may be considered for calculating the modulation energies.

In the same or another embodiment, only the signal frequencies contained below a predefined maximum signal frequency are considered. For example, only the signal frequencies are below about 40 HZ are considered.

Then, at step 18, an indicator of the signal-to-noise ratio of the biosignal is determined by the processor using the calculated amount of modulation energy for the biological activity and the calculated amount of modulation energy for the noise. In one embodiment, the indicator of the signal-to-noise ratio corresponds to the ratio between the amount of modulation energy for the biological activity and the amount of modulation energy for the noise. In another example, the indicator of the signal-to-noise ratio corresponds to the kurtosis of the biological signal. In a further embodiment, the indicator of the signal-to-noise ratio corresponds to the in-to-out of band spectral power of the biological signal.

At step 20, the determined indicator of noise level is outputted by the processor. For example, the indicator of noise level may be stored in memory such as a cache memory, or outputted by the communication unit to be displayed on a display unit.

It should be understood that the above-described method may be embodied as a system comprising at least one processor or processing unit, a memory or storing unit, and a communication unit for receiving and transmitting data. The memory comprises statements and instructions stored thereon that, when executed y the processor, performs the steps of the above-described method 10.

In one embodiment, the method 10 is embodied as a computer program product which comprises a computer readable memory storing computer executable instructions and statements thereon that, when executed by a processing unit, perform the steps of the method 10.

Figure 2:
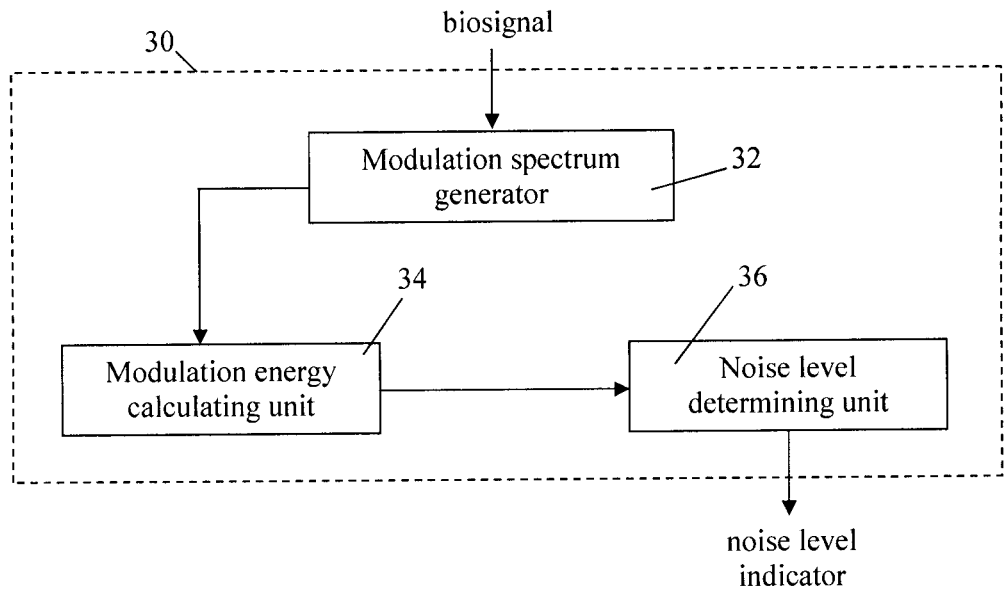
FIG. 2 is a block diagram illustrating a system for evaluating the quality of a biosignal, in accordance with an embodiment.

FIG. 2 illustrates one embodiment of a system 30 for evaluating a level of noise in a biosignal. The system 30 comprises a modulation spectrum generator 32, a modulation energy calculating unit 34, and a noise level determining unit 36. In one embodiment, the level of noise may be indicative of a signal-to-noise ratio (SNR). In another embodiment, the level of noise may be expressed as an index value such as the MS-IQ index described below. In a further embodiment, the level of noise is expressed as a percentage such as the ratio of the noise modulation power to the entire signal power expressed as a percentage.

The modulation spectrum generator 32 is adapted to receive a measured biosignal that corresponds to a time representation of a biological activity measured by an adequate sensor and determine a modulation spectrum for the time signal using the above-described method. The time biosignal comprises a first component representative of the biological activity, and a second and different component representative of the noise contained in the time biosignal. The modulation energy calculating unit 34 is adapted to receive the modulation spectrum from the modulation spectrum generator 32, and determine from the modulation spectrum a first amount of modulation energy corresponding to the biological activity component and a second amount of modulation energy corresponding to the noise component using the above-described method. The noise level determining unit 36 is adapted to receive the first and second amounts of modulation energy from the modulation energy calculating unit 34, determine an indicator of the level of noise from the first and second amounts of modulation energy, and output the indication of the level of noise, using the above-described method.

In one embodiment, the modulation spectrum generator 32, the modulation energy calculating unit 34, and the noise level determining unit 36 are independent from one another, and they are each provided with respective processing unit, internal memory, and communication unit. The internal memory of each one of the modulation spectrum generator 32, the modulation energy calculating unit 34, and the noise level determining unit 36 comprises statements and instructions stored thereon that, when executed by the respective processing unit, performs the respective steps of the method 10. In another embodiment, the modulation spectrum generator 32, the modulation energy calculating unit 34, and the noise level determining unit 36 are all part of a same device which comprises a processing unit, a memory, and communication means. In this case, the processing unit is adapted to execute all of the steps of the method 10.

Figure 3:
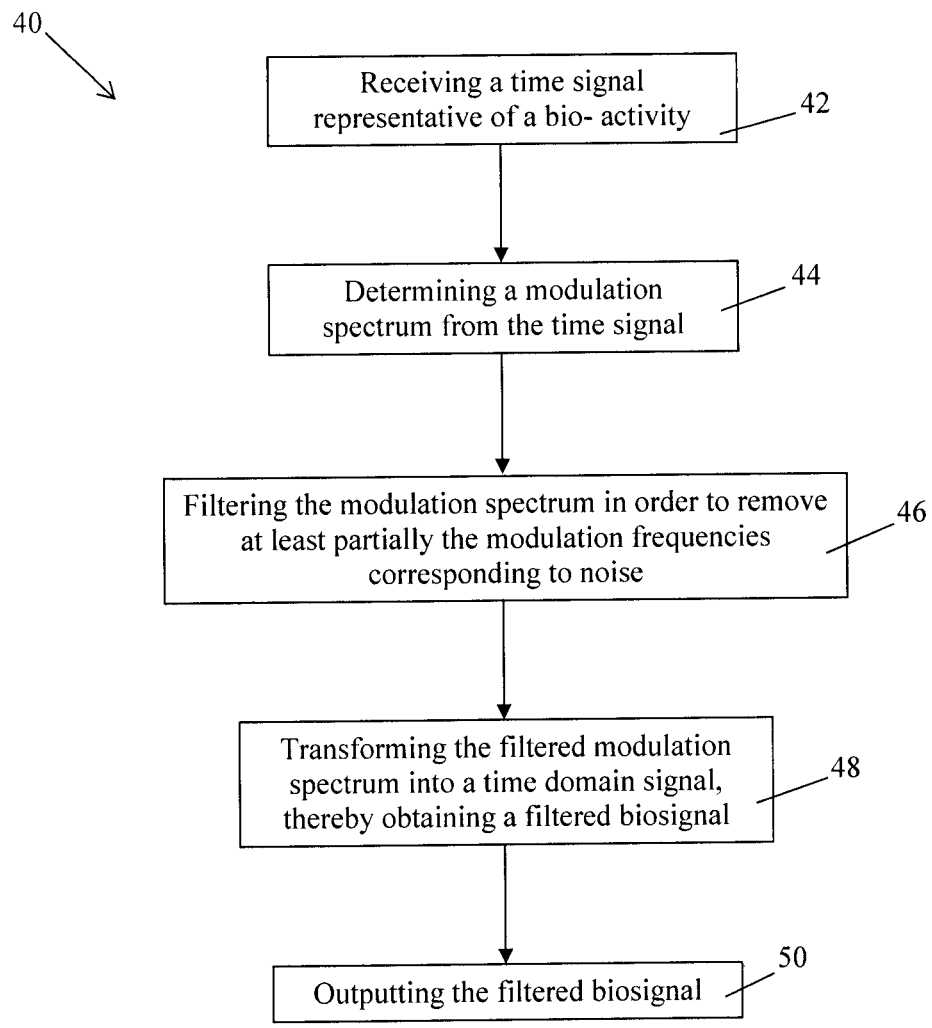
FIG. 3 is a flow chart of a method for filtering noise in a biosignal, in accordance with an embodiment.

FIG. 3 illustrates one embodiment of a computer-implemented method 40 for filtering the measurement of a biosignal in order to reduce the noise components contained therein, and therefore improve the signal-to-noise ratio of the biosignal. The method 40 is performed by at least one processor or processing unit that is connected to a memory and a communication unit for receiving and transmitting data.

At step 42, a measured biosignal, i.e. a time-domain signal of which the amplitude is representative of the amplitude of a biological activity measured by a sensor, is received by the processor via the communication unit. Then, the modulation spectrum of the time-domain signal is generated at step 44. The modulation spectrum is generated using the above-described method in reference to the method 10. For example, two different Fourier transforms may be successively applied to the time-domain biosignal in order to obtain its modulation spectrum. A first Fourier transform is applied to the time-domain signal in order to obtain a frequency-domain signal. Then, a second and different Fourier transform is applied across the time dimension of the frequency-domain signal to obtain the modulation spectrum, which corresponds to a frequency-frequency modulation representation of the biosignal.

At step 46, the modulation spectrum is filtered in order to remove at least partially the modulation frequencies corresponding to noise. In one embodiment, the filtering of the modulation spectrum reduces the frequency corresponding to at least some of the modulation frequencies associated with noise. In another embodiment, the filtering of the modulation spectrum suppresses at least some of frequencies corresponding to the modulation frequencies associated with noise. It should be understood that the filtering step may be performed digitally by a processor or by an electronic or analog filter.

In an embodiment in which the measured time-domain biosignal is an ECG signal, the modulation spectrum corresponding to the ECG signal comprises a plurality of frequency lobes substantially regularly spaced apart in modulation frequency, as described below. In this case, the modulation frequencies located outside the lobes such the frequencies located between adjacent lobes are considered as modulation frequencies associated with noise, and their corresponding frequency is to be at least reduced by the filtering process 46. In this case, a bandpass filter may be used to maintain the frequencies corresponding to the modulation frequencies contained within the lobes substantially unchanged while at least reducing the frequencies corresponding to the modulation frequencies associated with noise such as the modulation frequencies located between two adjacent lobes. It should be understood that more than one bandpass filter may be used to filter the modulation spectrum.

In one embodiment, the bandpass filter used for filtering the modulation spectrum may be adaptive over time to accommodate the variation over time of the modulation frequencies associated with the lobes due to the change of the heart rate over time. In one embodiment, the filter center frequencies substantially coincide with the beats per minute in Hz (i.e. 60 bpm=1 Hz) and its harmonics, and the bandwidth of the filters is substantially equal to about 1.25 Hz in the modulation domain.

While the present description refers to the use of at least one bandpass filter to filter a biosignal corresponding to a heart rate, it should be understood than other type of filter may be adequate for filtering a biosignal associated with a biological signal other than a heart rate. For example, lowpass filters, highpass filters, bandstop filters, and/or the like may be used.

Once the modulation spectrum has been filtered, the filtered modulation spectrum is transformed back into a time-domain signal, thereby obtaining a filtered time-domain biosignal.

In one embodiment, a first inverse Fourier transform is applied to the filtered modulation spectrum in order to obtain a filtered frequency domain representation, and a second inverse Fourier transform is applied to the filtered frequency domain representation, thereby obtaining the filtered time domain signal.

While the present description refers to the use of first and second Fourier transforms at step 44 in order to convert the time-domain biosignal into a frequency-domain signal and the frequency-domain signal into a frequency-frequency modulation signal, respectively, and the use of first and second inverse Fourier transforms at step 48 in order to obtain the filtered frequency domain representation and the filtered time domain signal, respectively, it should be understood that first and second transforms and first and second inverse transforms other than Fourier transforms may be used. Any adequate invertible first transform that may convert the time-domain biosignal into a frequency-domain signal may be used in replacement of the first Fourier transform. Similarly, any adequate invertible second transform that may convert a frequency-domain signal into a frequency-frequency modulation signal may be used in replacement of the second Fourier transform. It should be understood that the first and second inverse transform correspond to the inverse transform of the first and second transforms, respectively.

At step 50, the filtered time-domain biosignal is outputted. For example, the filtered time-domain biosignal may be locally stored in a storing unit or transmitted to an external storing unit to be stored thereon. In another example, the filtered time-domain biosignal may be sent to a display unit to be displayed.

While the above description refers to the filtering of an ECG biosignal, it should be understood that the same filtering method may be used to filter biosignals other than ECG signals such as other bio-electrical signals, e.g. electromyography signals and electroencephalography signals, bio-acoustic signals of which the amplitude is indicative of the amplitude of a sound of a human body such as breathing, heart sounds, or phonetic and non-phonetic utterances, biomechanical signals such as a mechanomyogram or a contact accelerometer vibrations signal, bio-optical signals such as a signal representing a movement of a being, and/or the like.

It should be understood that the above-described filtering method may be embodied as a system comprising at least one processor or processing unit, a memory or storing unit, and a communication unit for receiving and transmitting data. The memory comprises statements and instructions stored thereon that, when executed by the processor, performs the steps of the above-described filtering method.

In one embodiment, the above-described filtering method is embodied as a computer program product which comprises a computer readable memory storing computer executable instructions and statements thereon that, when executed by a processing unit, perform the steps of the above-described filtering method.

Figure 4:
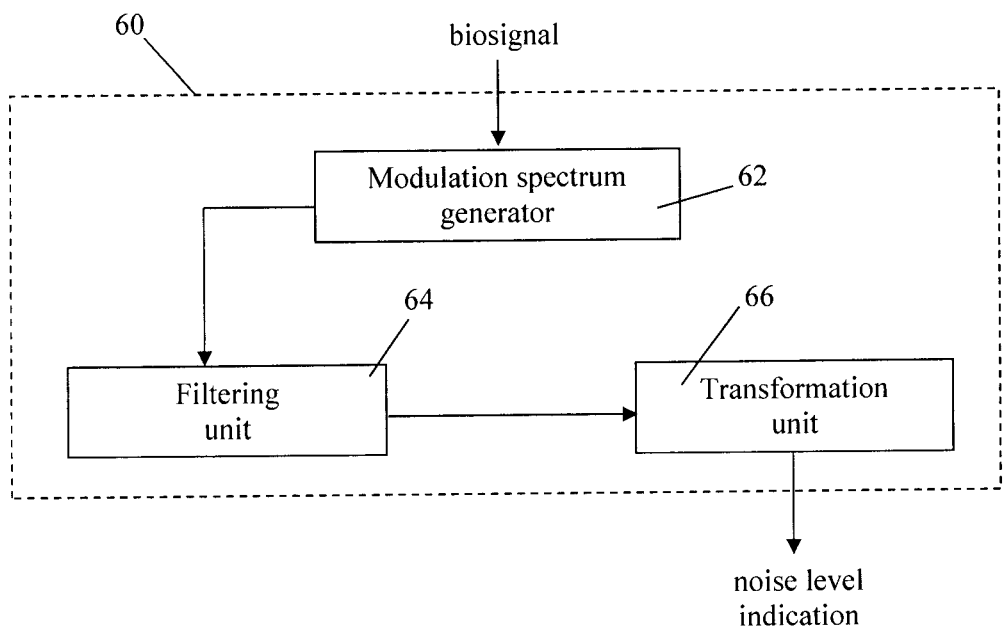
FIG. 4 is a block diagram illustrating a system for filtering noise in a biosignal, in accordance with an embodiment.

FIG. 4 illustrates a system 60 for filtering a biosignal in order to reduce the noise components contained therein, and therefore improve the signal-to-noise ratio of the biosignal. The system 60 comprises a modulation spectrum generator 62, a filtering unit 64, and a transformation unit 66.

The modulation spectrum generator 62 is adapted to receive a time biosignal representative of a biological activity and determine a modulation spectrum for the time signal using the above-described method. The time biosignal comprises a first component representative of the biological activity, and a second and different component representative of the noise contained in the time biosignal. The filtering unit 64 is adapted to receive the modulation spectrum from the modulation spectrum generator 62, and filter the received modulation spectrum in order to at least partially remove the noise components from the modulation spectrum, using the above-described method. The filtered modulation spectrum is then sent to the transformation unit 66 which converts it into a time-domain signal, i.e. the filtered biosignal, using the above-described method. The transformation unit 66 then outputs the filtered biosignal.

In one embodiment, the modulation spectrum generator 62, the filtering unit 64, and the transformation unit 66 are independent from one another, and they are each provided with a respective processing unit, internal memory, and communication unit. In this case, the memory of each one of the modulation spectrum generator 62, the filtering unit 64, and the transformation unit 66 comprises statements and instructions that, when executed by the respective processing unit, perform the respective steps. In another embodiment, the modulation spectrum generator 62, the filtering unit 64, and the transformation unit 66 are all part of a same device which comprises a processing unit, a memory, and communication means. In this case, the processing unit is adapted to execute all of the steps of the method 40.

In one embodiment, the method 40 is embodied as a computer program product which comprises a computer readable memory storing computer executable instructions thereon that when executed by a processing unit perform the steps of the method 40.

It should be understood that the biosignal may be received from a memory or storing unit in which the biosignal has been previously stored. The biosignal may also be directly received from the sensor that measures the biosignal.

It should also be understood that the biosignal may be generated by any adequate measuring device adapted to measure the biological activity corresponding to the biosignal. In another example, the biosignal may be a synthesized signal. In this case, the biosignal do not correspond to a signal measured on a body.

In the following, there is described an exemplary application of the method 10 for calculating an ECG quality index based on the rate-of-change of ECG short-term spectral magnitude components, a signal representation commonly termed "modulation spectrum". The motivation lies in the fact that the ECG will have spectral components which change at different rates relative to conventional ECG artifacts. As such, within this modulation spectral domain ECG components can be separated from all other noise sources, thus allowing for "blind" measurement of the ECG signal-to-noise ratio (SNR). In one embodiment, the developed metric that is adaptive to the user's heart rate can operate with single-lead systems, and does not rely on classifier training or QRS detection. Moreover, the metric is shown to outperform two conventional benchmark quality indices across four datasets covering both synthesized and recorded ECGs, as well as ECGs collected from healthy and pathological patients. As such, the proposed metric may be shown to be an ideal candidate for emerging remote patient monitoring and wireless body area network (WBAN) applications.

The remainder of the present description is organized as follows. Section I describes the materials and methods used in this study, including a description of the modulation spectral signal representation, its motivation for ECG quality assessment, the proposed MS-QI measure, and the experimental setup. Experimental results are then presented in Section II and discussed in Section III. Finally, conclusions are drawn in Section IV.

I. METHODS AND MATERIALS

In this section, there is presented the modulation spectral representation and the proposed quality index is described. The datasets used, a description of two benchmark algorithms, and the measures used to gauge system performances are also presented.

A. ECG Modulation Spectral Representation

Figure 5:
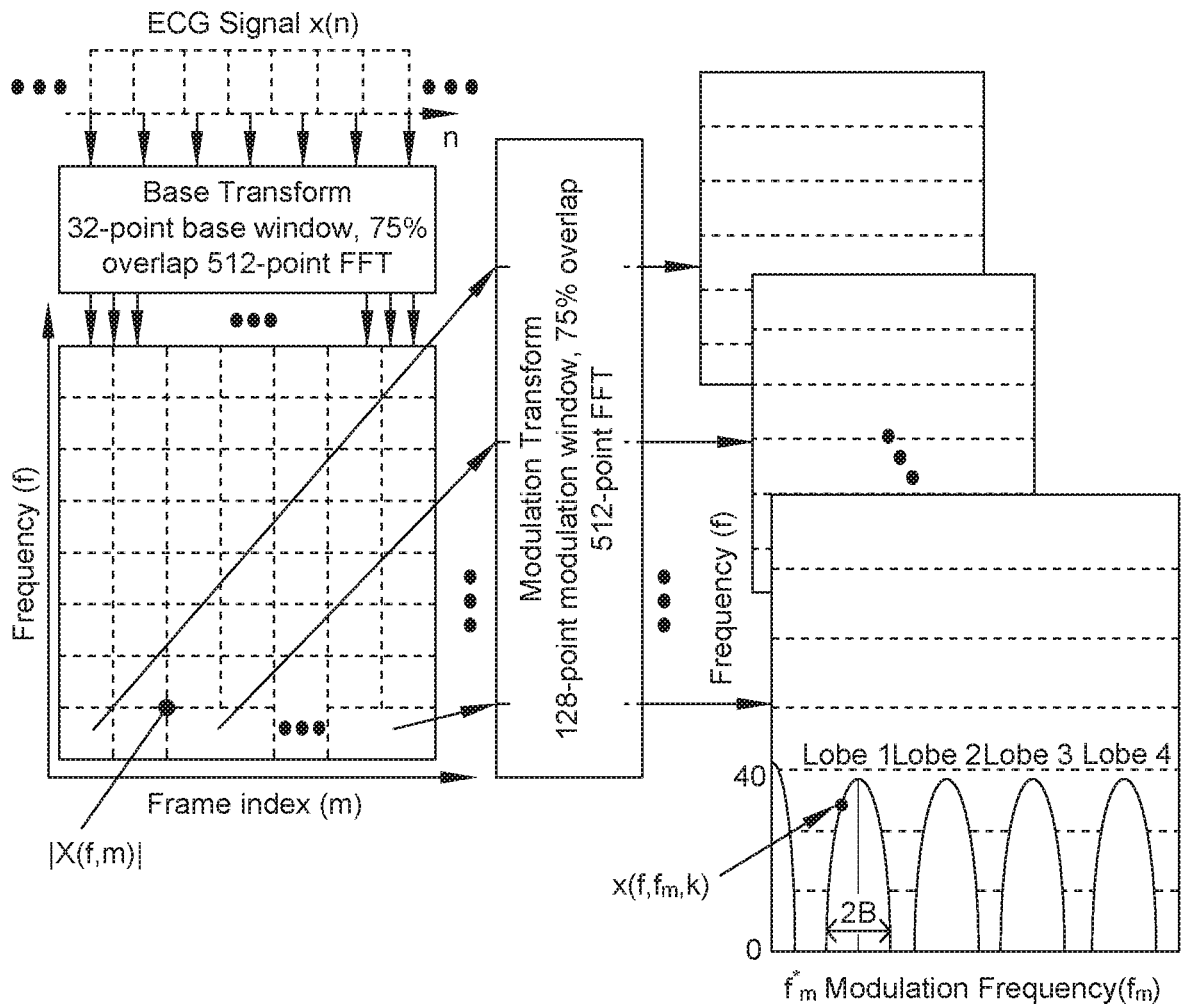
FIG. 5 schematically illustrates the transformation of a time domain signal into a modulation spectrum, in accordance with an embodiment.

FIG. 5 illustrates the signal processing steps involved in the computation of the modulation-spectral representation. The sampled ECG signal x(n) is first windowed and transformed via a 512-point fast Fourier transform (FFT), for example, resulting in the conventional time-frequency representation (or spectrogram). In our experiments, a sample rate of 256 Hz, 32-point windows, and 75% overlap are used. It should be understood that other adequate configurations may be used. Spectral magnitude components |X(f, m)| (for frame index m) are then processed by a second 512-point FFT across the time-axis to result in a final frequency-frequency representation called the modulation spectrogram. In our experiments, 128-point windows are used with 75% overlap—the equivalent of analyzing 4 seconds of ECG data (128×0.03125 s). The representation is given by $\chi(f, f_m, k)$, where f corresponds to conventional frequency, $f_m$ to modulation frequency, and k is the frame index for the second transform.

In one embodiment, the options for base and modulation window sizes, as well as overlap rates are optimized using training synthesized clean ECG data and they impose a limitation on the minimum duration of a test ECG to be of about four seconds. In the experiments, we have found that reducing the modulation window to 64 points (thus reducing the ECG duration limitation to about 2 seconds), for example, causes a slight decrease in metric performance (around about 2%). As such, the measure may still be further fine-tuned for alternate applications requiring fast responses, such as in intensive care units.

In essence, modulation frequencies quantify the rate-of-change of different ECG frequency components. The motivation here lies in the fact that ECG signals will have spectral components which change at different rates relative to conventional ECG artifacts, thus improving signal-noise separability in the modulation domain.

Figure 6A:
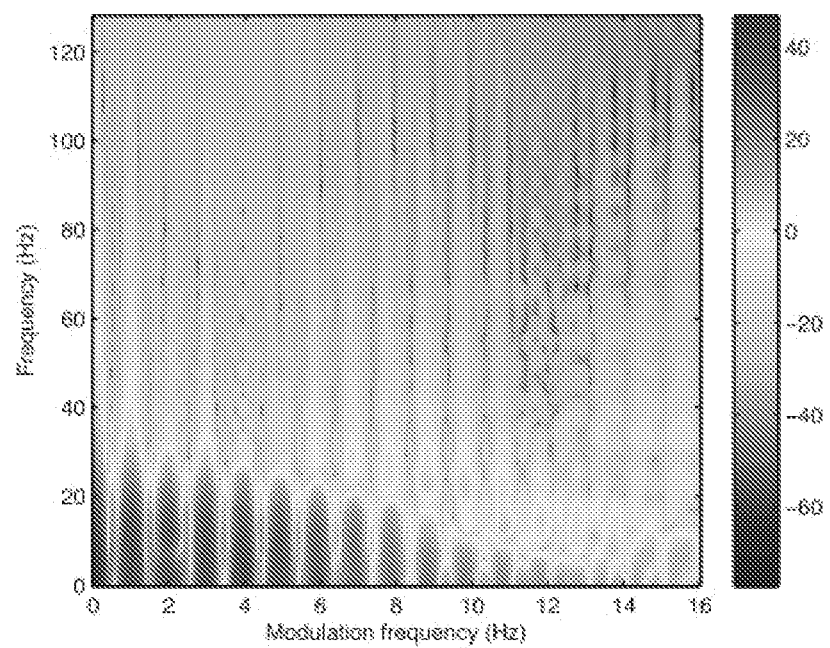
FIG. 6a illustrates an exemplary modulation spectrogram of a synthesized clean ECG with 60 bpm, in accordance with an embodiment.
Figure 6B:
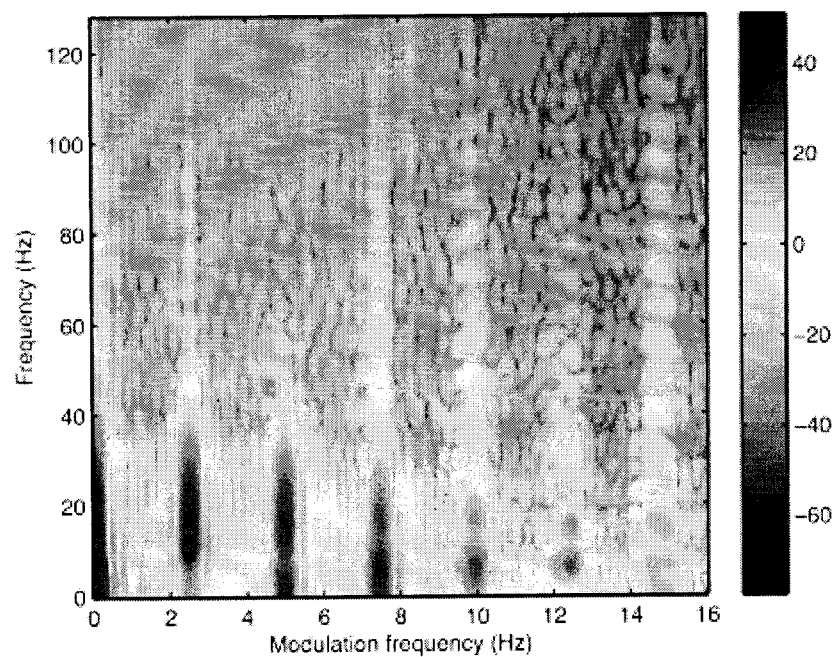
FIG. 6b illustrates an exemplary modulation spectrogram of a synthesized clean ECG with 150 bpm, in accordance with an embodiment.
Figure 6C:
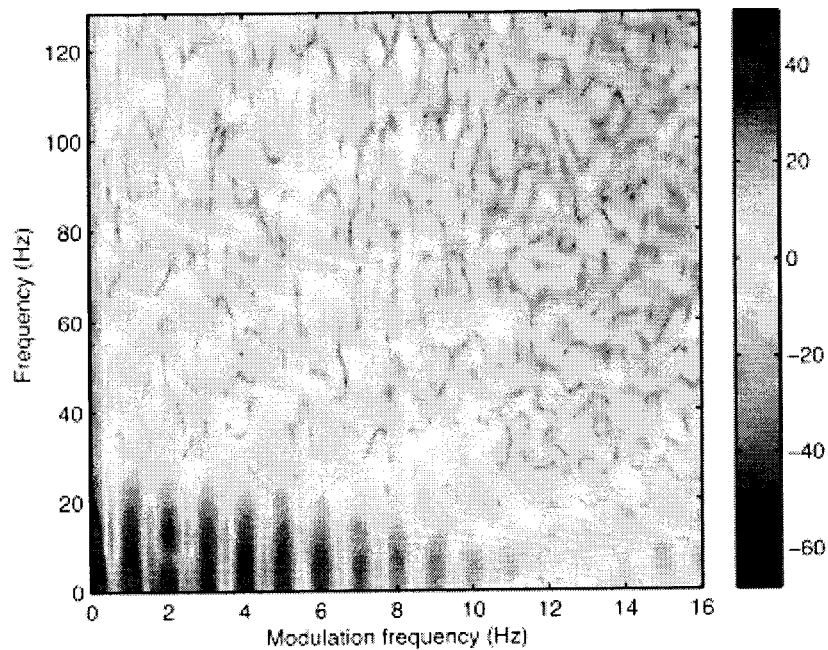
FIG. 6c illustrates an exemplary modulation spectrogram of a synthesized noisy ECG with a signal-to-noise ratio of 5 dB and with 60 bpm, in accordance with an embodiment.

In order to motivate the use of the modulation domain for ECG quality assessment, FIGS. 6a and 6b illustrate exemplary average modulation spectrograms of synthetic clean ECG signals with 60 and 150 beats per minute (bpm), respectively (averaged over 2 minutes of ECG data). As can be seen from two subfigures, the majority of the signal energy is below a frequency of about 40 Hz. For the first scenario, i.e., 60 bpm, it can be seen that the ECG spectral components change with a rate of $f_m$=about 1 Hz, as well as several other harmonics. In the case of 150 bpm, spectral components change with a rate of $f_m$=about 2.5 Hz, along with its harmonics. FIG. 6c, in turn, shows a noisy synthetic ECG signal (with an SNR=5 dB and 60 bpm) that has been corrupted by several noise components taken from the MIT-BIH Noise Stress Test Database. As can be seen, frequency components around $f_m$=about 0 Hz (i.e., stationary components) are of wider bandwidth (f> about 10 Hz) than their clean counterparts; modulation frequency "lobes" and their harmonics are diminished; and modulation frequencies between lobes are amplified. Notwithstanding, despite the low SNR, ECG components can still be clearly seen in the modulation spectrogram, with clear lobes still being detectable up to $f_m$=about 8 Hz, as opposed to about 10-12 Hz in the clean ECG scenario. These insights have motivated us to develop an ECG quality index, as detailed next.

B. Modulation Spectrum Based Quality Index

From FIGS. 6a-6c, it can be seen that ECG and noise components behave differently in the so-called modulation spectrum domain. ECG components appear in "modulation frequency lobes" centered in modulation frequencies related to the heart rate and its harmonics and are confined to lie between 0≤f≤ about 40 Hz. Noise components, on the other hand, do not follow such patterns and can affect several modulation frequencies, particularly $f_m$=0 Hz due to the stationary properties of some noise sources. Using these insights, there is developed a modulation spectral-based ECG quality index that is akin to a signal-to-noise ratio measure.

To compute the measure, the first "lobe" needs to be detected within each per-frame modulation spectrogram X(f, $f_m$, k), thus corresponding to the user's heart rate. To this end, first the per-frame modulation spectrogram is normalized to unit energy, thus resulting in $X_n$ (f, $f_m$, k). The energy is then computed for each normalized modulation frequency bin between about 0.8≤$f_m$≤ about 3 Hz (thus covering heart rates from about 50-about 200 bpm) and averaged over the 0≤f≤ about 40 Hz range. The modulation frequency bin $f^*_m$ with the highest average normalized energy is selected as the center of the first lobe. For the purpose of quality assessment, we have found experimentally that the first five lobes provide an accurate representation of the ECG signal components and that each lobe has a bandwidth of about 0.625 Hz, thus resulting in the ECG modulation energy (EME) measure for frame k:

$$EME(k) = \sum_{j=1}^{5} X_n(f \mid_0^{40}, jf^*_m - B \leq jf^*_m \leq jf^*_m + B, k), \quad \text{Eq. 1}$$

where $f|_0^{40}$=0≤f≤ about 40 and B=0.3125 Hz.

It should be understood that the range of modulation frequency comprised between 0.8 Hz and 3 Hz is exemplary only. This specific range of modulation frequency has been chosen since only the heart rate values contained between 50 bpm and 200 bpm have been chosen for the purpose of the present analysis. It should be understood that the range of modulation frequency considered may change if another range of heart rate is to be analyzed.

The assumption here is that EME parameter represents the information available from the actual ECG components and that everything outside the first four lobes will correspond to noise/artifacts. As such, the per-frame modulation spectral based quality index (MS-QI) is given as the ratio of EME to the remaining modulation energy (RME), i.e.:

$$MS - QI(k) = \frac{EME(k)}{RME(k)}. \quad \text{Eq. 2}$$

where RME is found as the difference between the total energy in the modulation spectrogram and EME. The final quality index MS-QI is given as the average MS-QI(k) over all frames in the recorded ECG signal. While the metric is not mathematically bound between [0,1], we have observed experimentally that MS-QI values are typically between 0 and about 1.5, with higher values corresponding to improved quality.

C. Dataset 1: Synthetic ECG Data

We used the ecgsyn Matlab™ function available in Physionet™ to generate synthetic ECG signals. The function allows for several user-settable parameters, such as mean heart rate, sampling frequency, waveform morphology (i.e., P, Q, R, S, and T timing, amplitude, and duration), standard deviation of the RR interval, and the low-frequency (LF) to high-frequency (HF) ratio. For the experiments described herein, 200 signals of 120-second duration were generated by randomly sampling two input parameters: heart rate (uniformly sampled between about 50 and about 180 beats per minute) and LF/HF ratio (uniformly sampled between about 0.5 and about 8.9). The heart rate range was chosen to cover certain heart illnesses (e.g., tachycardia), as well as different physical activity levels (e.g., resting, walking, running). The LF/HF ratio range, in turn, covers wakefulness, rapid eye movement, light-to-deep sleep, and myocardial infarction. Variation of other ecgsyn input parameters may also be considered.

In order to investigate the usefulness of the above-described method for evaluating the level of noise of a biosignal, the above-mentioned clean synthesized ECG signals were corrupted by several noise sources at known SNR levels. In one embodiment, three types of artifacts are commonly present in ECG signals: environmental, experimental, and physiological. The first type can be originated from the main powerline interference, electromagnetic interference, and from the circuit components themselves. The second type is due to undesired changes in the experimental setup, such as human error or user motion. Such artifacts are difficult to remove as they overlap in time and frequency with the desired ECG signal. Lastly, physiological artifacts are those generated by other physiological processes in the body, such as muscle artifacts or baseline wander due to breathing modulation.

Figure 7:
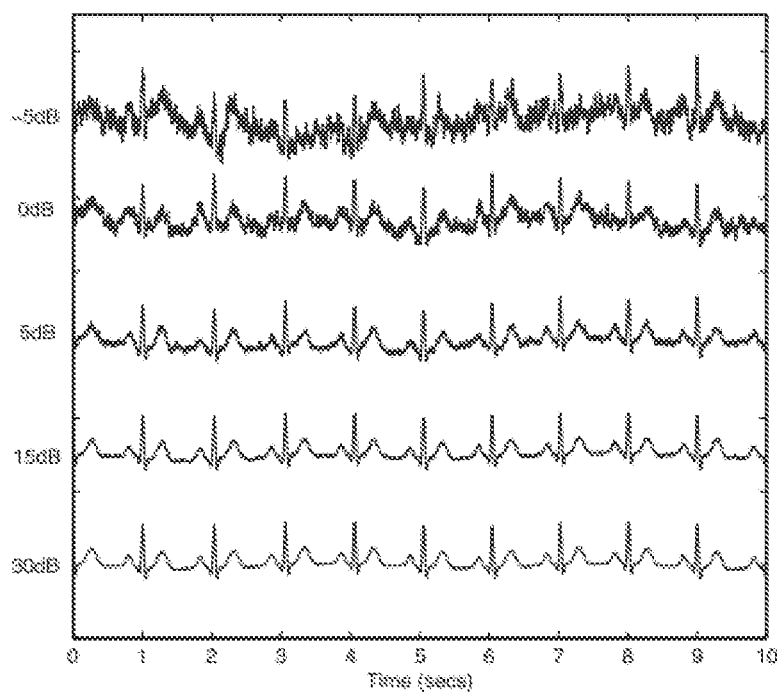
FIG. 7 presents exemplary ten-second excerpts from different noisy synthetic ECG signals, in accordance with an embodiment.

For the experiments described herein, recorded electrode motion artifacts, baseline wander noise, and muscle artifacts were taken from the MIT-BIH Noise Stress Test Database and used to corrupt the clean synthetic ECGs. Two other types of noise sources were also added, namely pink (commonly used to model observation noise) and Brownian noise (used to model electrode movement artifacts). Powerline interference is not investigated as notch filters have been extensively used in the literature for this purpose. Noisy signals were generated at SNRs of −5 dB, 0 dB, 5 dB, 15 dB, and 30 dB. FIG. 7 illustrates exemplary 10-second excerpts of the generated noisy signals. Overall, a total of 40 hours of ECG data (clean and noisy) is available for testing.

D. Dataset 2: Recorded Hexoskin™ Garment ECG Data

Figure 8:
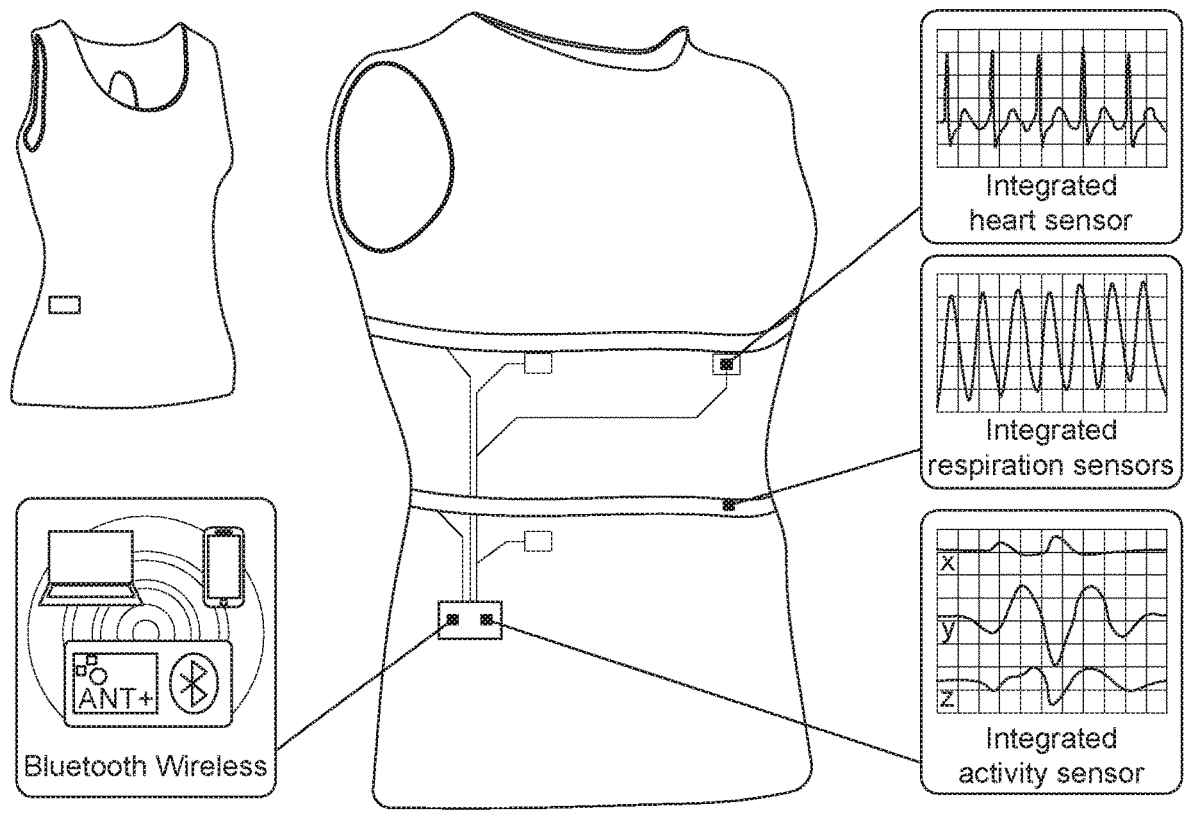
FIG. 8 illustrates an Hexoskin™ garment used to collect ECG data during three different activity levels, in accordance with an embodiment.
Figure 9A:
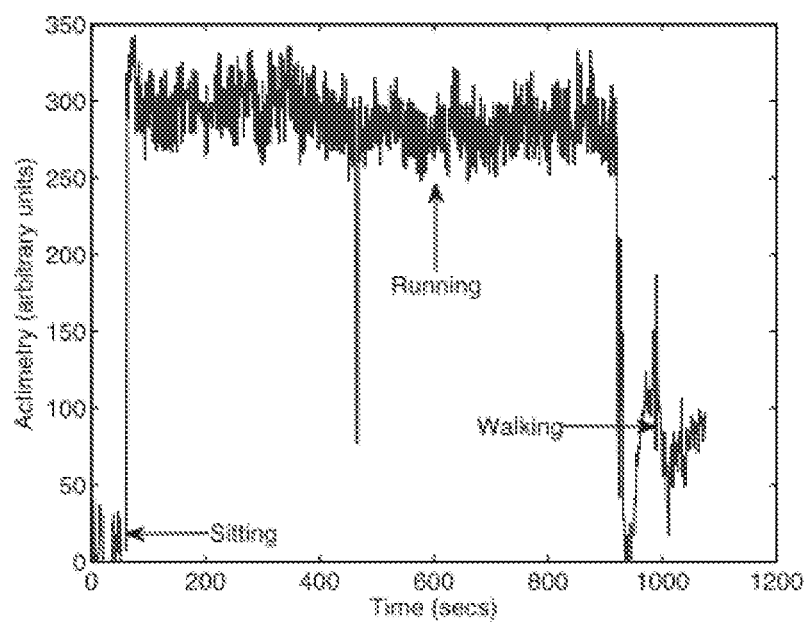
FIG. 9a presents an exemplary actimetry profile for an ECG recording with the Hexoskin™ garment of FIG. 8.
Figure 9B:
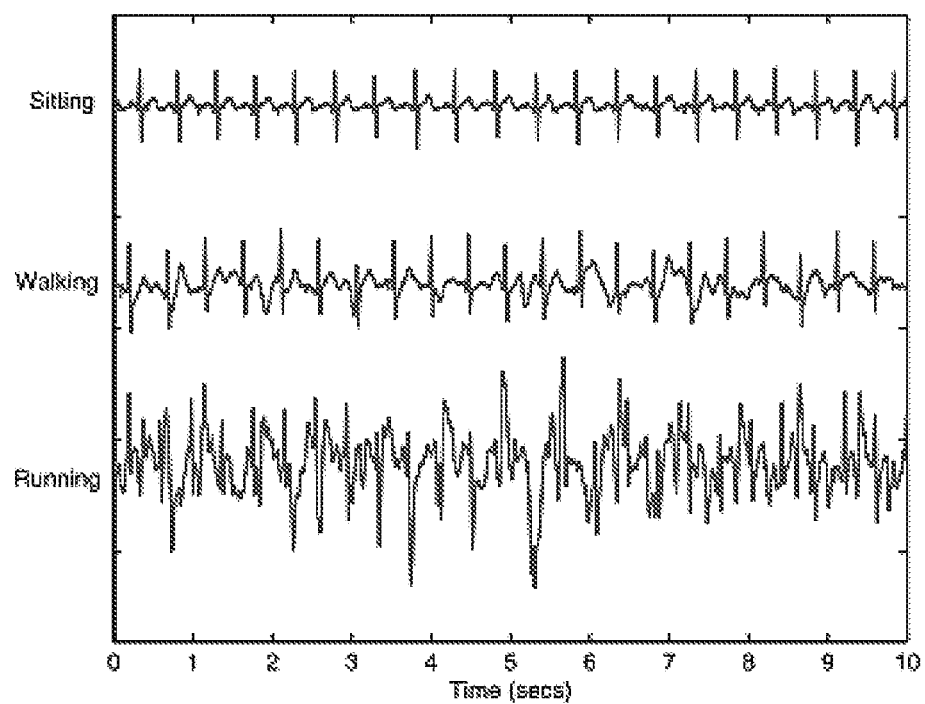
FIG. 9b presents 10-second excerpts of exemplary collected signals during (top to bottom) sitting, walking, and running, in accordance with an embodiment.
Figure 9C:
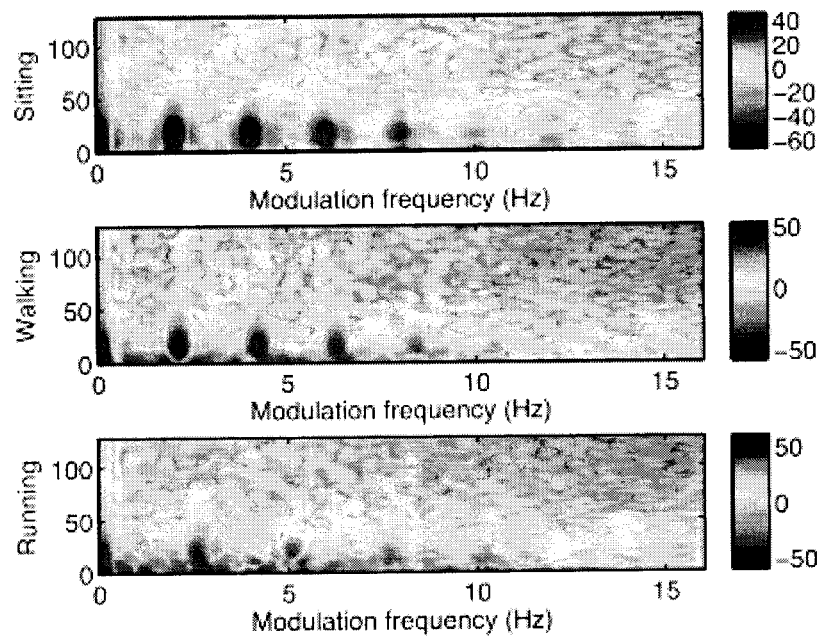
FIG. 9c illustrates exemplary modulation spectrograms for the collected signals of FIG. 9b.

To test the developed quality metric on real recorded data, we use the Hexoskin™ smart shirt which is equipped with textile ECG, breathing, and 3-D accelerometry sensors, as illustrated in FIG. 8. Single-channel ECG signals are collected with about 256 Hz sample rate and about 12-bit resolution. The Hexoskin™ transmits data to smart devices via secure Bluetooth, thus is an ideal candidate for telehealth applications which could greatly benefit from an objective quality index. Here, data is recorded from three users wearing the Hexoskin™ during three different activity levels: sitting, walking and running. FIG. 9a illustrates an actimetry profile measured via the device's accelerometry sensors and shows the experimental protocol used: approximately 1-minute sitting (actimetry level: 0-50 arbitrary units), followed by 15-minutes running (actimetry level: 250-350) and lastly a 3-minute walk (actimetry level: 50-150). Actimetry levels are given every one second. FIGS. 9b and 9c, in turn, depict 10-second excerpts of the ECG data collected during the three activity levels, as well as their respective modulation spectrograms. As can be clearly seen from the two subplots, actimetry values are inversely proportional to quality (i.e., higher activity level, lower ECG quality). Overall, roughly one hour of data is available for testing.

E. Dataset 3: Physionet Challenge Signal Quality Database

To further test the proposed algorithm, a subset of the publicly available Physionet/Computing in Cardiology 2011 Challenge dataset was used. Data consisted of 12-lead ECG collected at a 500 Hz sample rate using conventional ECG machines. The overall quality over the 12 leads were then manually annotated by a group of 23 volunteers, roughly half experienced and half inexperienced with ECG readings, and later categorized as "acceptable" or "unacceptable". Here, 100 acceptable and 100 unacceptable 10-second single-lead recordings were randomly pre-selected and down-sampled to 256 Hz. Since a final overall acceptability rating was given over the 12-leads (e.g., by majority vote, if most leads were acceptable, the entire 12-lead signal was deemed acceptable), we found that some of the randomly selected single-channel 'acceptable' signals were actually unacceptable and vice-versa. As such, two raters visually inspected the 200 single-lead signals and re-labelled them. Overall, the raters were in agreement on 142 of the total 200 signals, thus the experiments described herein are based on 71 acceptable and 71 unacceptable signals, for a total of 24 minutes of ECG data available for testing.

F. Dataset 4: Recorded Ambulatory ECG Data

Lastly, we were interested in testing if MS-QI would be suitable for pathological ECG recordings, thus validating its use for remote telehealth operation. To this end, we used the well-known Physionet MIT-BIH Arrhythmia Database. Data is comprised of two-channel ambulatory ECG recordings collected from 47 cardiology patients (sampled at 360 Hz). The data was analyzed independently by two cardiologists who annotated the readings with beat, rhythm, and signal quality labels. Regarding the latter, segments of the recordings that were deemed noisy by the annotators were labeled as "noisy," whereas the remaining segments are deemed to be clean. For our experiments, 62 clean and 65 noisy ECG segments of 2-minute duration were used after downsampling to 256 Hz, thus totaling 4 hours and 14 minutes of data available for testing.

G. Benchmark Quality Measures

For performance comparison purposes, two widely-used benchmark measures are used. The first is the ECG sample kurtosis ($\kappa$), or the fourth-order moment, which measures the peakedness of the signal and is given by:

$$\kappa = \frac{\frac{1}{N}\sum_{i=1}^{N}(x(i)-\bar{x})^4}{\left(\frac{1}{N}\sum_{i=1}^{N}(x(i)-\bar{x})^2\right)^2}, \qquad \text{Eq. 3}$$

where $\bar{x}$ is the sample mean of $x(n)$ and N are the number of ECG data points. The kurtosis value increases as the signal quality increases. A threshold is set such that $\kappa \geq 5$ is assumed for high quality ECG.

The second metric is the in-band (i.e., 5-40 Hz) to out-of-band spectral power ratio (IOR) in the QRS complex. The measure assumes that the majority of the ECG spectral power in the QRS complex will be between 5-40 Hz. Assuming our 256 Hz sample rate, the IOR metric is defined as:

$$IOR = \frac{\int_{5}^{40} X(f)df}{\int_{0.05}^{1.28} X(f)df - \int_{5}^{40} X(f)df}, \qquad \text{Eq. 4}$$

where $X(f)$ corresponds to the ECG power spectrum. Higher IOR values are expected for better quality ECG signals. In one embodiment, the proposed MS-QI metric may be seen as an extension of the IOR metric, in the sense that it also looks for ratios of ECG and "non-ECG" components, but with the advantage of having access to a richer pool of information via the modulation frequency content.

H. Performance Assessment

To assess the effectiveness of the proposed and benchmark measures on the first two datasets, two performance figures-of-merit are used, namely the Pearson and Spearman rank correlations. Pearson correlation $\rho$ measures the linear relationship between two variables $q(n)$ and $t(n)$ and is given by:

$$\rho = \frac{\sum_{i=1}^{N}(q(i)-\bar{q})(t(i)-\bar{t})}{\sqrt{\sum_{i=1}^{N}(q(i)-\bar{q})^2 \sum_{i=1}^{N}(t(i)-\bar{t})^2}} \qquad \text{Eq. 5}$$

where $\bar{q}$ and $\bar{t}$ are the sample averages of q and t, respectively.

Here, $q(n)$ represents the estimated quality indices given either by the proposed metric or the two benchmark measures. The variable $t(n)$, in turn, represents the true quality value and is given here as either the SNR value in the synthetic ECG case (Dataset 1) or the actimetry level in Dataset 2. In the latter case, since only three activity levels are present, estimated quality values are computed for a series of 5-second excerpts of the recorded data within each activity type. All investigated metrics are positively correlated with SNR and negatively correlated with actimetry levels. The second metric, Spearman rank correlation ($\rho_s$), measures how well the quality indices rank against the "true" quality indicators (e.g., SNR and activity level). The $\rho_s$ metric is calculated using (5) but with the original data values replaced by the ranks of the data value. A reliable quality indicator will have $\rho$ and $\rho_s$ close to unity. For the third and fourth datasets, in turn, since only "acceptable" and "unacceptable" (or "noisy" and "clean") labels are available, we use the overlap in distributions between the two classes as a figure of merit. In essence, a smaller overlap indicates greater class separability, thus a better quality index. A two-sample Kolmogorov-Smirnov test is used to statistically quantify the separability of the two distributions. Overall, 45 hours and 38 minutes of ECG data are used in our analyses.

TABLE I

Performance comparison between proposed MS-QI measure and the two benchmark metrics for Datasets 1 and 2.

| Dataset | Map | MS-QI $\rho$ | MS-QI $\rho_s$ | $\kappa$ $\rho$ | $\kappa$ $\rho_s$ | IOR $\rho$ | IOR $\rho_s$ |
|---|---|---|---|---|---|---|---|
| 1 | — | 0.95 | 0.93 | 0.90 | 0.93 | 0.93 | 0.97 |
|   | Log | 0.90 | 0.93 | 0.89 | 0.93 | 0.94 | 0.97 |
| 2 | — | −0.94 | −0.92 | −0.81 | −0.92 | −0.71 | −0.89 |
|   | Log | −0.90 | −0.92 | −0.92 | −0.92 | −0.83 | −0.89 |

II. RESULTS

Figure 10A:
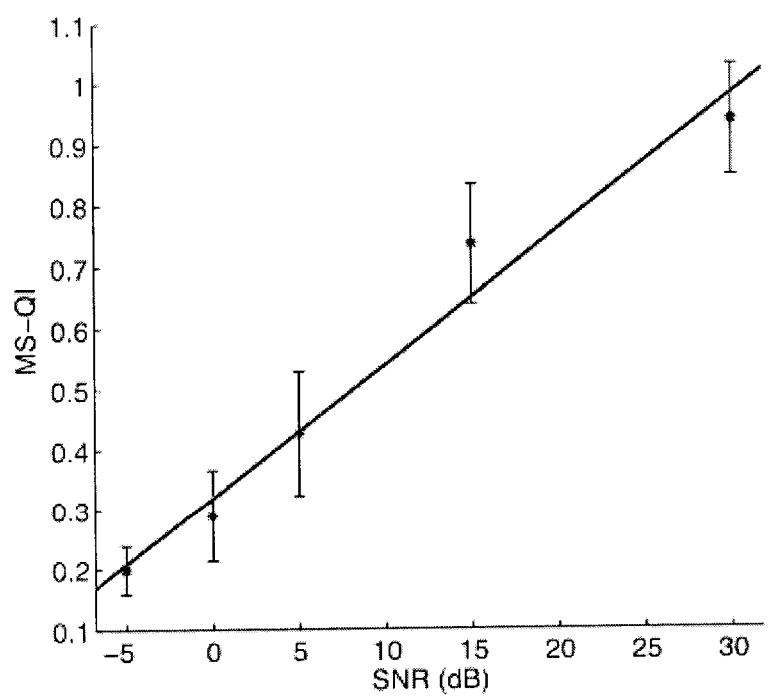
FIGS. 10a-10c illustrate exemplary scatterplots and errorbars of an MS-QI, a κ, and an IOR, respectively, as a function of SNR for Dataset 1.
Figure 10B:
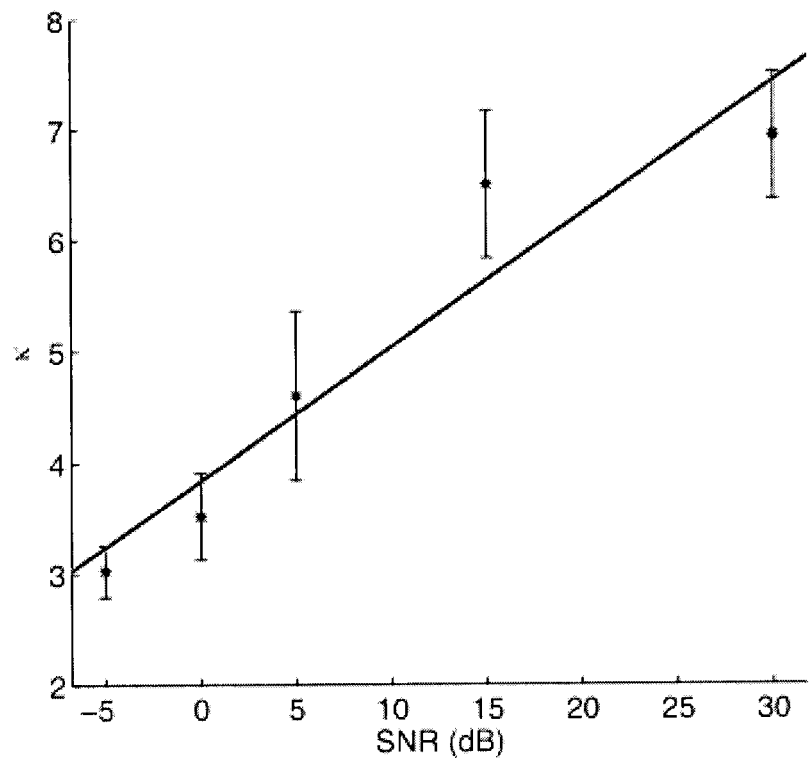
Figure 10C:
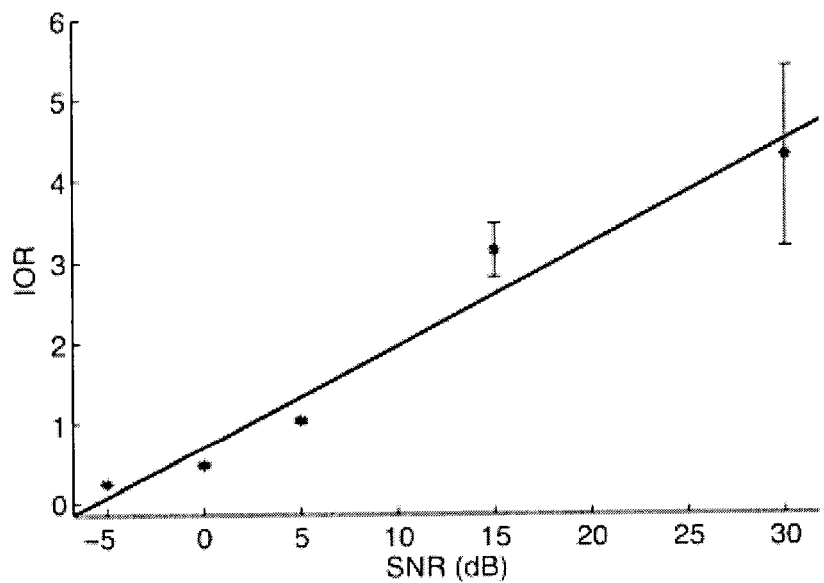
Figure 11A:
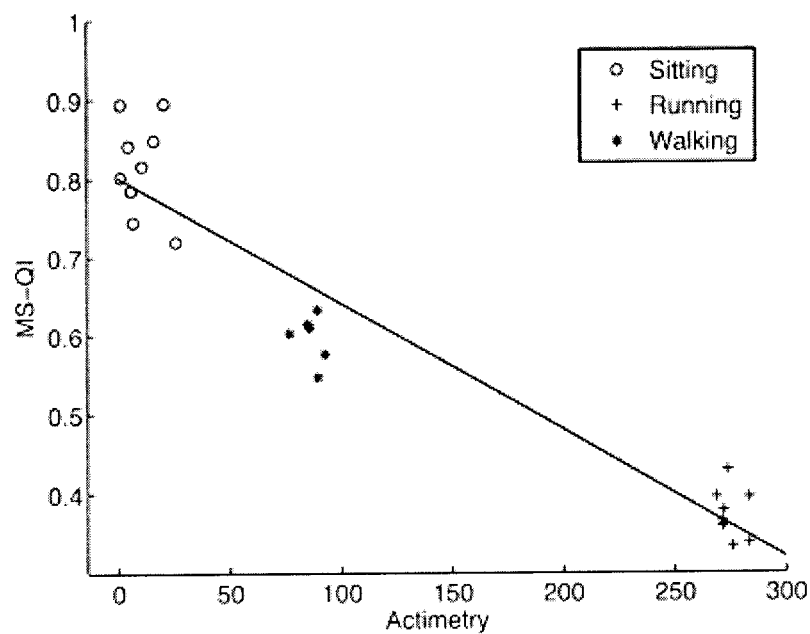
FIGS. 11a-11c illustrate exemplary scatterplots of an MS-QI, a κ, and an IOR, respectively, as a function of activity level (actimetry) for Dataset 2.
Figure 11B:
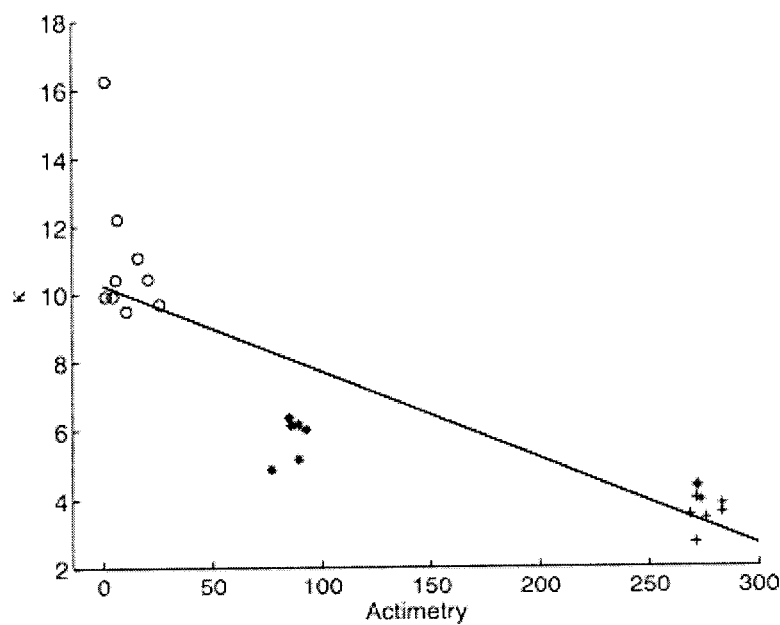
Figure 11C:
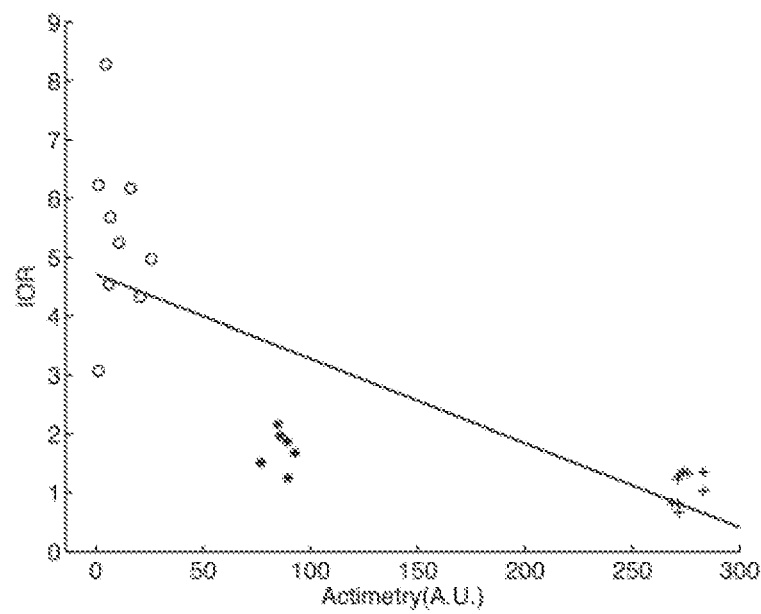

Table I shows the performance obtained with the proposed and the two benchmark metrics for Datasets 1 and 2. For Dataset 1, the correlations are between the obtained metrics and the SNR values for all 1000 signals (200 signals×5 SNR levels). For Dataset 2 the correlations are between the obtained metrics and actimetry levels. The scatterplots depicted by FIGS. 10a-10c show the behaviour of the MS-QI, κ, and IOR metrics, respectively, as a function of SNR for the synthetic ECG signals. To avoid cluttering, only the average metric values per SNR are shown, along with their standard deviations. Moreover, FIGS. 11a-11c show the behaviour of the MS-QI, κ, and IOR metrics as a function of actimetry level for Dataset 2. To avoid cluttering, only nine 5-second excerpts per activity level are presented. As can be seen, a logarithmic behaviour is present, thus the performances in Table I are listed both without and with a logarithmic mapping.

Figure 12:
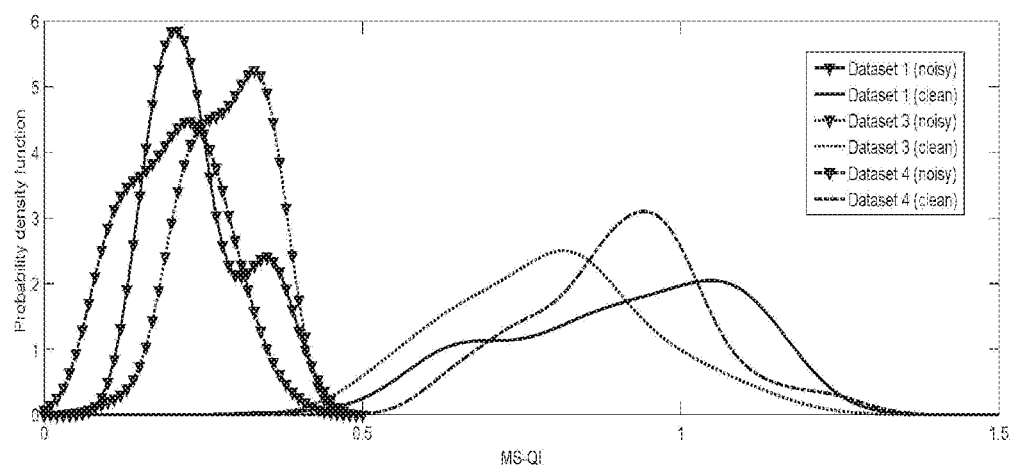
FIG. 12 illustrates an exemplary Kernel fit of MS-QI probability distributions for good (black) and bad (gray) quality ECG for Datasets 1 (solid), 3 (dash), and 4 (dash-dot)
Figure 13A:
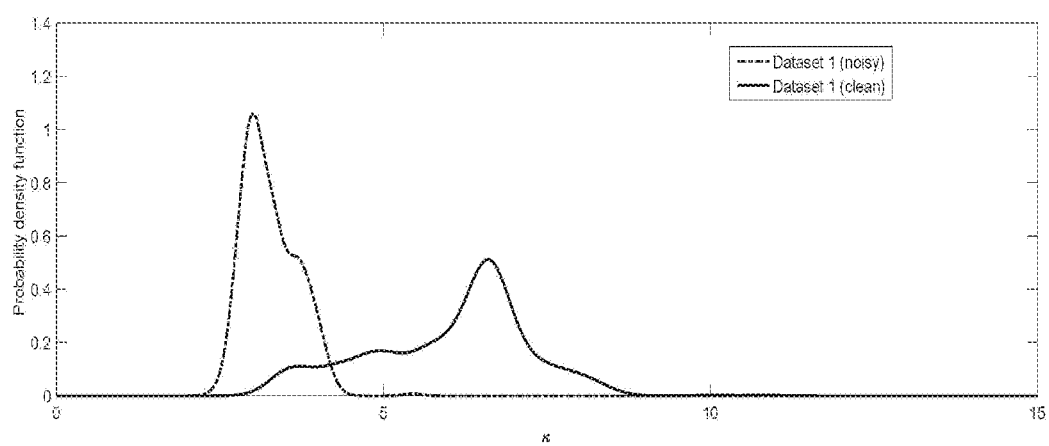
FIG. 13a-13b illustrate Kernel fit of κ probability distributions for good (black) and bad (gray) quality ECG for Dataset 1 and Datasets 3 (dash) and 4 (dash-dot), respectively.
Figure 13B:
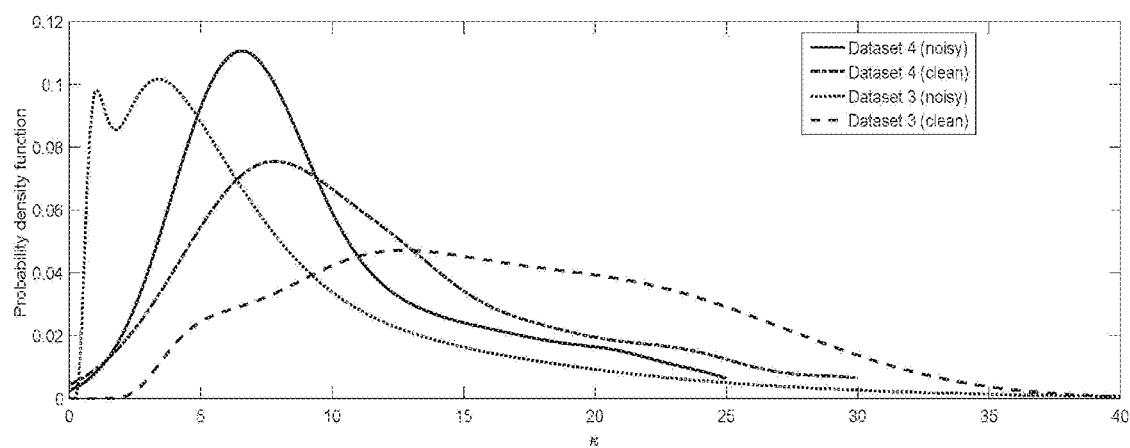

Lastly, for Datasets 3 and 4 we use the overlap in distributions between the clean (acceptable, good quality) and noisy (unacceptable, bad quality) ECG recordings as a figure of merit. For the MS-QI metric, kernel fits for the probability distributions are depicted by FIG. 12, where dark black curves correspond to clean recordings and light gray curves to noisy ones. Dashed lines are for Database 3 and dotted lines for Database 4. For comparison purposes, clean synthetic ECG data are represented by the solid black lines and noisy synthetic (i.e., SNR≤15 dB) data by gray solid lines. For the sake of brevity, comparisons are only performed for the κ benchmark metric as it performed more consistently across Datasets 1 and 2, relative to the IOR benchmark (see Table I). FIGS. 13a and 13b show the kernel fits for the probability distributions for Datasets 1, as well as 3 and 4, respectively. As previously, black lines correspond to good quality ECG and gray lines to bad quality recordings.

III. DISCUSSION

Figure 14:
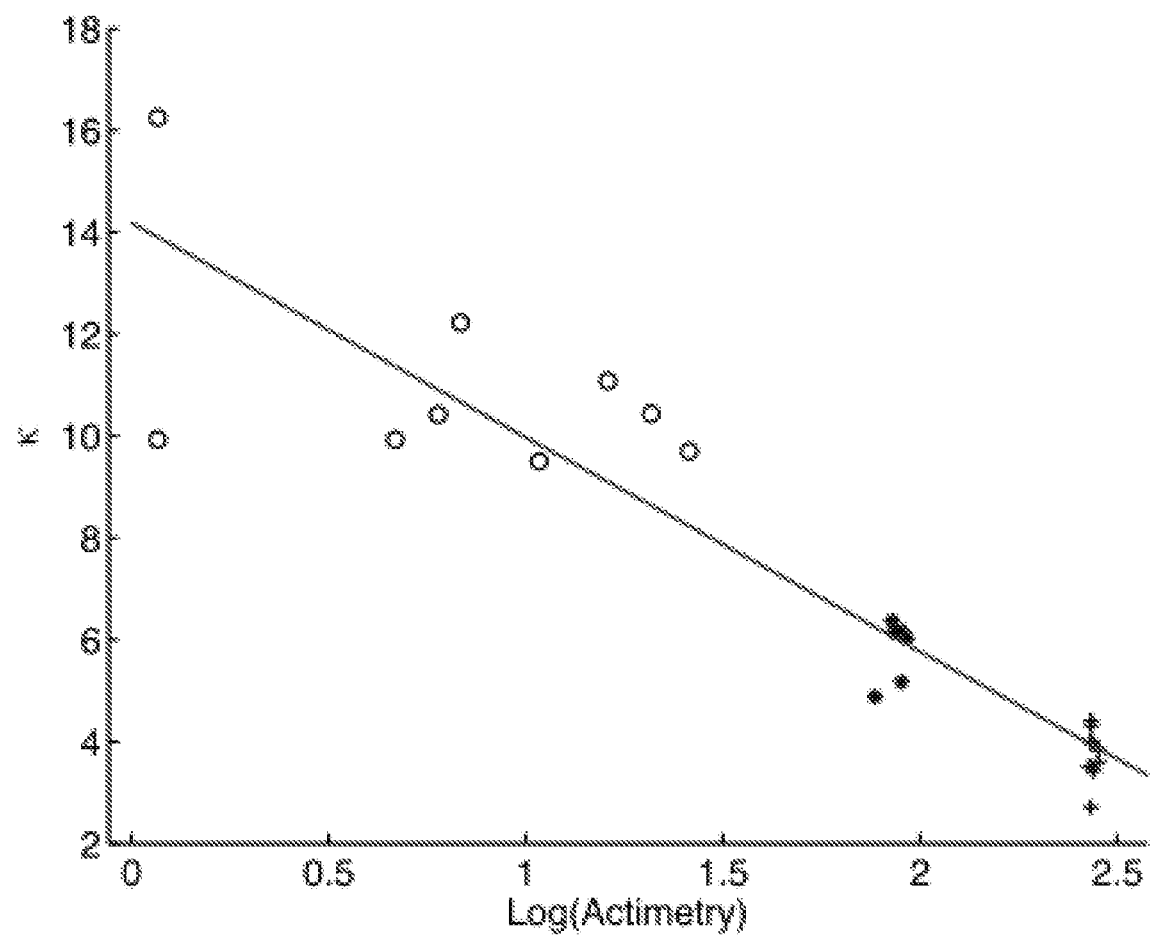
FIG. 14 illustrates a scatterplot of κ as a function of log(actimetry) for Dataset 2.

From Table I, it can be seen that the proposed MS-QI metric outperforms the two benchmark algorithms on Datasets 1 and 2 in terms of the ρ performance metric. Relative to the $\rho_s$ metric, it achieved results equal to κ on both datasets and outperformed the IOR metric on Dataset 2. The IOR metric, on the other hand, achieved the highest $\rho_s$ on Dataset 1. Overall, the consistency of the MS-QI metric across the two Datasets suggests that it may be more suitable not only for remote telehealth applications, but also for athletic training applications where the ECG data is highly contaminated with movement artifacts. In fact, if we compare the scatterplot for the MS-QI metric in FIG. 11a to that of the κ benchmark versus log(actimetry) in FIG. 14, it can be observed that the discrimination between the three activity levels, particularly between the walking and running conditions, remains higher for the proposed quality index, thus also suggesting potential applications as an activity type detector for context-aware WBANs. Interestingly, of the three activity conditions explored with Dataset 2, sitting was the one that showed the highest variability, particularly for the benchmark metrics. This could be an artifact from the data collection protocol, as sitting was the first activity performed during data collection and textile ECG coupling may have been lower due to lack of moisture and sweat. Moreover, the performance gains relative to the IOR metric across the two datasets show the importance of the modulation spectral information for the development of a blind SNR-like measure for ECG signals. As mentioned above, the proposed MS-QI measure achieved comparable results with the κ benchmark, particularly for the $\rho_s$ metric. The benefits of the proposed MS-QI metric, however, become more apparent from the data collected in real-world settings, such as from Datasets 3 and 4. From FIG. 12, it can be seen that the overlap in probability distributions between the good and bad ECG signals was minimal for the MS-QI metric, with a clear boundary between the two conditions at MS-QI=0.5. This finding remained true not only for the recorded datasets, but also for the synthetic ECG, thus showing the robustness of the proposed metric to ECG type (recorded/synthetic) as well as patient condition (healthy/pathological). The κ metric, on the other hand, showed to be sensitive to ECG type with significant differences in probability distributions between synthetic (FIG. 13a) and recorded ECGs (FIG. 13b). While the κ=5 boundary between the two conditions could be seen with the synthetic ECGs, it increased to nearly 10 with the recorded data. This behaviour may be due to the sensitivity of the fourth order moment to outliers in the noisy signals, which may be misinterpreted as beats in clean ECG recordings. Moreover, the κ metric showed a very high overlap in probability distributions for Dataset 4, thus limiting its use for quality monitoring of pathological ECGs. To quantify this separability statistically, a two-sample Kolmogorov-Smirnov test was used. For the κ parameter, the difference between the two distributions was deemed insignificant, (p=0.11), whereas the separability was highly significant for the proposed MS-QI measure ($p<10^{-30}$).

V. CONCLUSION

In this paper, an innovative ECG quality index termed MS-QI was proposed based on modulation spectral insights. Using the new signal representation, ECG and noise components become more separable in the new modulation domain, thus allowing for a reliable quality measure to be developed. Experimental results showed the proposed measure outperforming two widely-used benchmark quality measures, namely ECG sample kurtosis and the QRS complex 'in-band to out-of-band' spectral power ratio, on synthesized ECGs, recorded healthy ECG, as well as recorded pathological ECGs. The proposed metric showed to be more reliable than the benchmark algorithms on four distinct datasets and its behaviour remained stable regardless of ECG type (synthetic vs. recorded), ECG recording mode (textile vs. conventional vs. ambulatory) and patient health (normal vs. pathological ECG). These findings suggest that the developed metric is a potential candidate not only for remote patient monitoring applications that involve patients being mobile and active, but also for athlete monitoring and activity type detection for context-aware WBANs.

While in the above description, the first five lobes are used for determining the level of noise of the biosignal, it should be understood that the number of lobes considered may vary. For example, Table II presents the performances when the number of lobes considered is varied. The best results are obtained when five lobes are considered. As indicated in Table II, the greatest ρ and $\rho_s$ are obtained for the synthetic data when five lobes are considered, and the greatest ρ and second greatest $\rho_s$ are obtained for the measured data when five lobes are considered.

TABLE II

Performances obtained when the number of lobes considered varies.

| ECG type | N = 1 lobe | | N = 2 lobes | | N = 3 lobes | | N = 4 lobes | | N = 5 lobes | |
|---|---|---|---|---|---|---|---|---|---|---|
| | $\rho$ | $\rho_S$ | $\rho$ | $\rho_S$ | $\rho$ | $\rho_S$ | $\rho$ | $\rho_S$ | $\rho$ | $\rho_S$ |
| Synthetic | 0.84 | 0.86 | 0.86 | 0.87 | 0.90 | 0.90 | 0.93 | 0.92 | 0.93 | 0.94 |
| Real | −0.68 | −0.77 | −0.89 | −0.84 | −0.94 | −0.91 | −0.94 | −0.92 | −0.92 | −0.93 |

In the following, there is presented experimental results obtained using the above-described method 40 for filtering a biosignal. The filter applied to the modulation spectrum of the biosignal comprises a bank of five adaptive bandpass filters, i.e. five adaptive linear-phase finite impulse response (FIR) filters. The center frequencies of the filters are adaptive over time, as the modulation frequencies of the lobes vary over time with the heart rate of the user. As described above, the main lobe is found at the modulation frequency having the greatest amount of energy between 0 Hz and about 40 Hz and located within the following modulation frequency range, i.e. between about 0.8 Hz and about 3 Hz, thus covering heart rates from about 50 bpm and 200 bpm.

Figure 15:
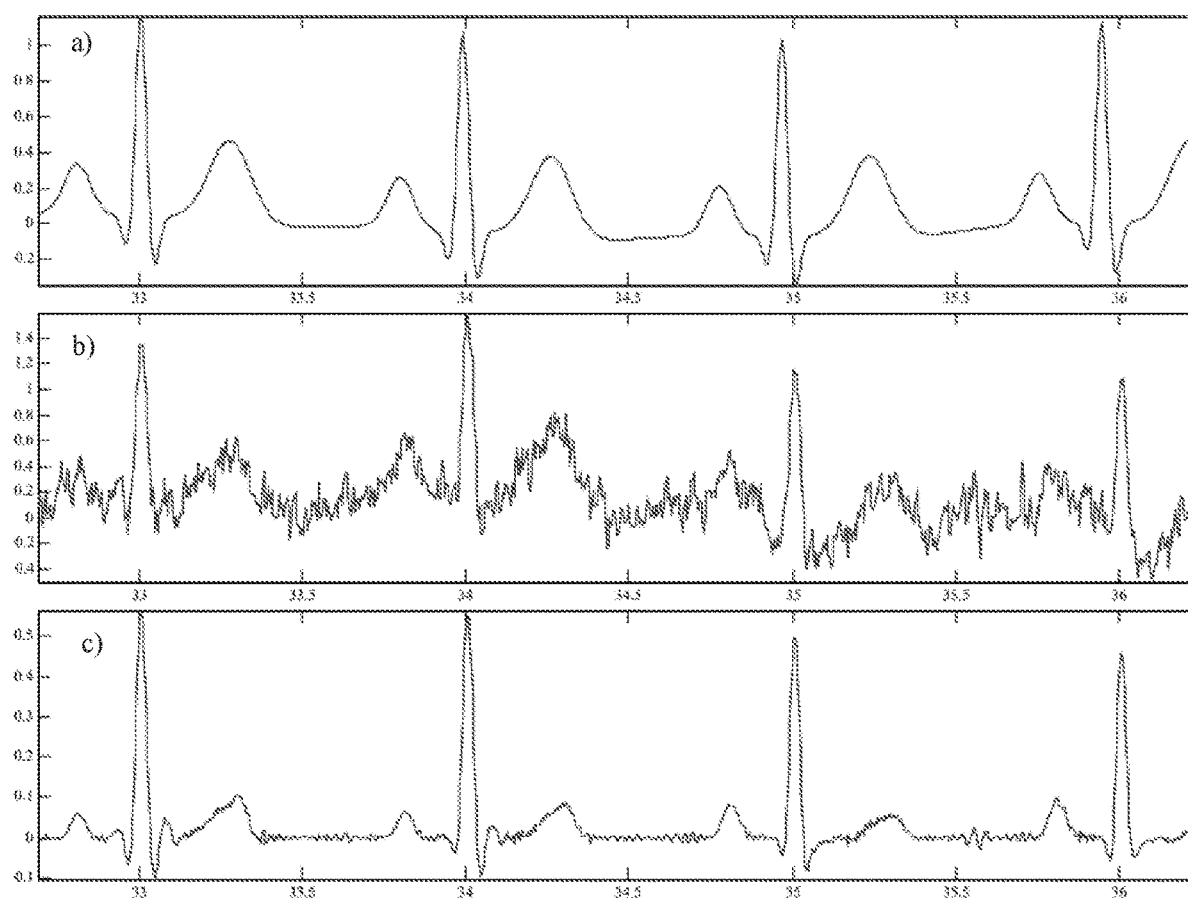
FIG. 15a illustrates an exemplary clean synthetic ECG, in accordance with an embodiment.
FIG. 15b illustrates an exemplary noisy ECG signal with a signal-to-noise ratio of 0 dB, in accordance with an embodiment.
FIG. 15c illustrates a denoised signal obtained when the method of FIG. 3 is applied to the noisy signal of FIG. 15b, in accordance with an embodiment.

FIGS. 15a-15c illustrate the denoising of a synthetized and noisy biosignal. FIG. 15a illustrates a time-domain synthetized biosignal representing the amplitude of a heart rate in time. FIG. 15b illustrates the synthetized signal of FIG. 15a to which noise has been added. The SNR of the biosignal of FIG. 15b is about 0 dB. FIG. 15c illustrates the denoised biosignal resulting from the application of the method 40 of the biosignal of FIG. 15b. As it may be seen, the application of the method 40 allows for reducing the noise contained in the noisy biosignal, and therefore improve its SNR.

Figure 16:
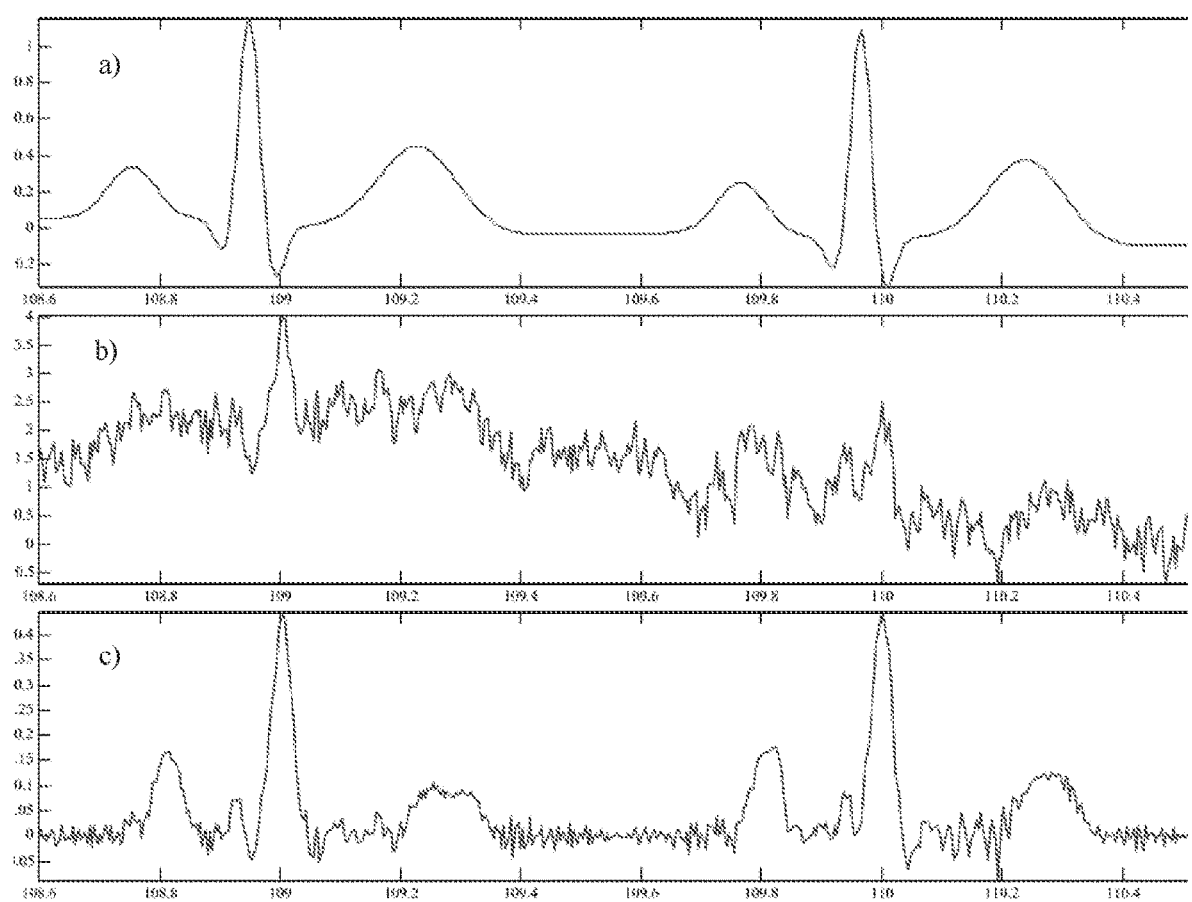

FIGS. 16a-16c illustrate the denoising of a synthetized and noisy biosignal. FIG. 16a illustrates a time-domain synthetized biosignal representing the amplitude of a heart rate in time. FIG. 16b illustrates the synthetized signal of FIG. 16a to which noise has been added. The SNR of the biosignal of FIG. 16b is about −10 dB. FIG. 16c illustrates the denoised biosignal resulting from the application of the method 40 of the biosignal of FIG. 16b. As it may be seen, the application of the method 40 allows for reducing the noise contained in the noisy biosignal, and therefore improve its SNR. The peaks of the biosignal can be detected from the denoised signal of FIG. 15c whereas it could not reliably be done in FIG. 15b before denoising.

Figure 17:
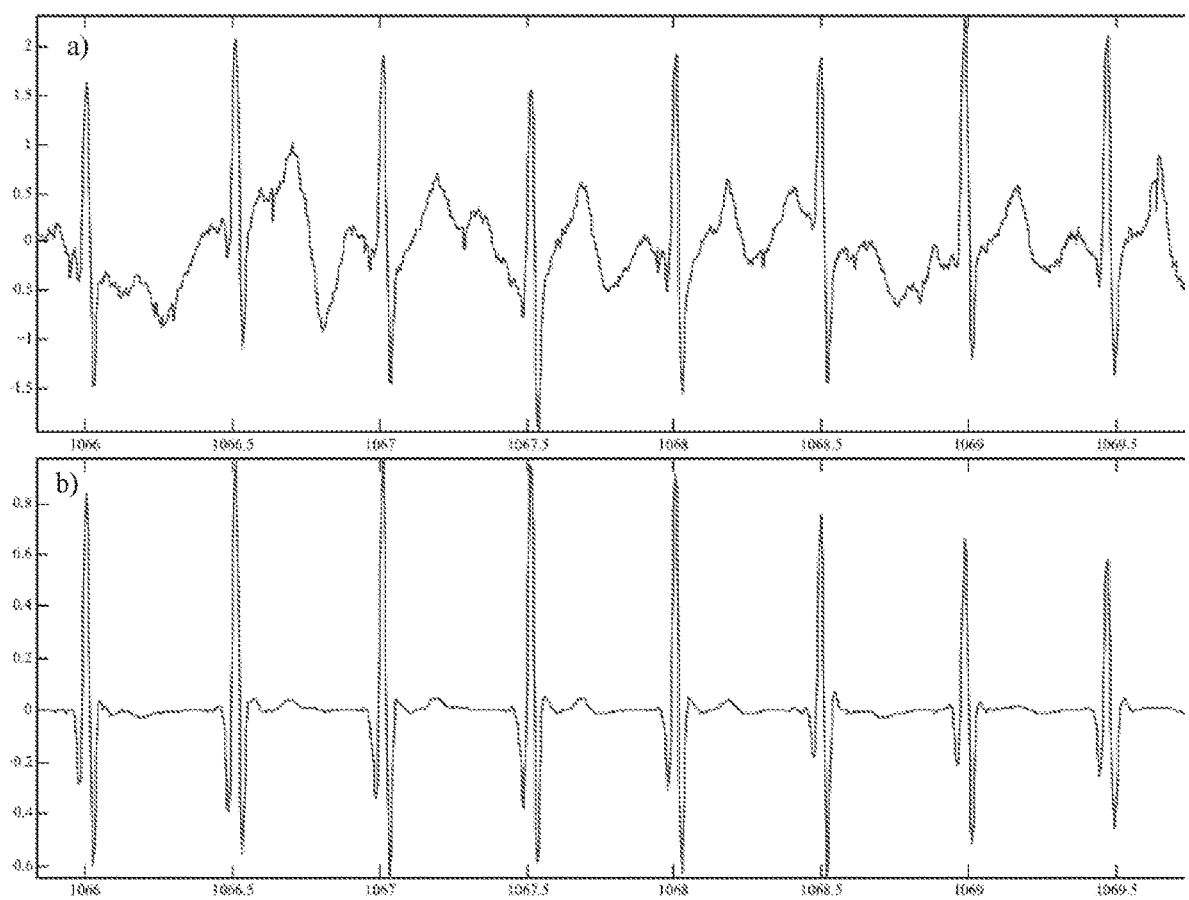
FIG. 17a illustrates an exemplary noisy but usable ECG signal, in accordance with an embodiment.
FIG. 17b illustrates a denoised signal obtained when the method of FIG. 3 is applied to the noisy signal of FIG. 17a, in accordance with an embodiment.
Figure 18:
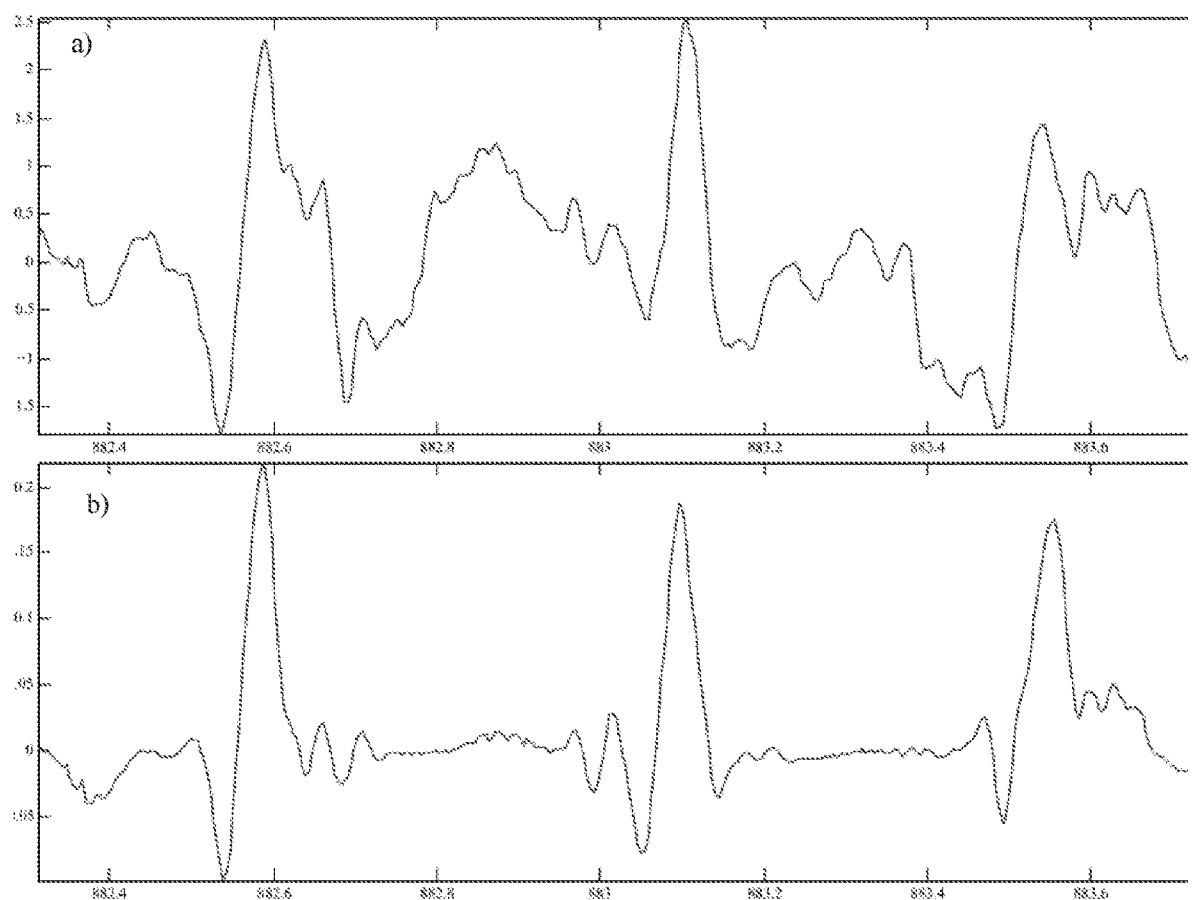
FIG. 18a illustrates an exemplary noisy and problematic ECG signal, in accordance with an embodiment.
FIG. 18b a denoised signal obtained when the method of FIG. 3 is applied to the noisy signal of FIG. 18a, in accordance with an embodiment.

FIG. 17a presents a noisy but usable biosignal representing the amplitude of a heart rate in time. The biosignal of FIG. 17a has been measured on a human body using the Hexoskin™. FIG. 17b presents the biosignal of FIG. 14a after being filtered using the method 40. FIG. 18a illustrates a noisy and problematic biosignal measured using the Hexoskin™ and FIG. 18b presents the biosignal of FIG. 18a after being denoised using the method 40.

The embodiments of the invention described above are intended to be exemplary only. The scope of the invention is therefore intended to be limited solely by the scope of the appended claims.

We claim:

1. A computer-implemented method for evaluating a level of noise in a biosignal, the method comprising:
   receiving a time signal representative of a biological activity, the time signal comprising a biological activity component and a noise component;
   determining a modulation spectrum for the time signal, the modulation spectrum representing a signal frequency as a function of a modulation frequency;
   determining, from the modulation spectrum, a first amount of modulation energy corresponding to the biological activity component and a second amount of modulation energy corresponding to the noise component
   determining an indication of the level of noise using the first and second amounts of modulation energy; and
   outputting the indication of the level of noise;
   wherein said determining the modulation spectrum comprises:
      applying a first transform to the time signal, thereby obtaining a time frequency representation of the time signal; and
      applying a second transform across a time dimension of the time frequency representation, thereby obtaining the modulation spectrum.

2. The method of claim 1, wherein said determining the first amount of modulation energy comprises:
   identifying lobes within the modulation spectrum corresponding to the biological activity component; and
   calculating the modulation energy corresponding to the lobes.

3. The method of claim 2, wherein said determining the second amount of modulation energy comprises calculating an amount of modulation energy contained between the lobes within the modulation spectrum.

4. The method of claim 2, wherein said identifying lobes comprises identifying lobes within at least one of a predefined range of modulation frequency and a predefined range of signal frequency.

5. The method of claim 1, wherein said determining an indication comprises calculating a ratio between the first and second amounts of modulation energy, thereby obtaining a quality index indicative of a signal-to-noise ratio.

6. A system for evaluating a level of noise in a biosignal, the system comprising:
   a spectrum generator of receiving a time signal representative of a biological activity and determining a modulation spectrum for the time signal, the modulation spectrum representing a signal frequency as a function of a modulation frequency, the time signal comprising a biological activity component and a noise component;
   an energy calculating unit for determining from the modulation spectrum a first amount of modulation energy corresponding to the biological activity component and a second amount of modulation energy corresponding to the noise component; and
   a noise level determining unit for determining an indication of the level of noise using the first and second amounts of modulation energy and outputting the indication of the level of noise;

wherein the spectrum generator is adapted to:
  apply a first transform to the time signal in order to obtain a time frequency representation of the time signal; and
  apply a second transform across a time dimension of the time frequency representation in order to obtain the modulation spectrum.

7. The system of claim 6, wherein, in order to obtain the first amount of modulation energy, the modulation energy calculating unit is adapted to:
  identify lobes within the modulation spectrum corresponding to the bio-electrical activity component; and
  calculate the modulation energy corresponding to the lobes.

8. The system of claim 7, wherein the modulation energy calculating unit is adapted to calculate an amount of modulation energy contained between the lobes within the modulation spectrum in order to obtain the second amount of modulation energy.

9. The system of claim 7, wherein the modulation energy calculating unit is adapted to identify lobes within at least one of a predefined range of modulation frequency and a predefined range of signal frequency.

10. The system of claim 6, wherein the noise level determining unit is adapted to calculate a ratio between the first and second amounts of modulation energy, thereby obtaining a quality index indicative of the level of noise.

11. A method for filtering noise in a biosignal, the method comprising:
  receiving a time signal representative of a biological activity, the time signal comprising a biological activity component and a noise component;
  determining a modulation spectrum for the time signal, the modulation spectrum representing a signal frequency as a function of a modulation frequency;
  filtering the modulation spectrum in order to remove at least partially the modulation frequencies corresponding to noise;
  transforming the filtered modulation spectrum into a time domain signal, thereby obtaining a filtered time domain biosignal; and
  outputting the filtered time domain biosignal;
  wherein said determining the modulation spectrum comprises:
    applying a first transform to the time signal, thereby obtaining a time frequency representation of the time signal; and
    applying a second transform across a time dimension of the time frequency representation, thereby obtaining the modulation spectrum.

12. The method of claim 11, wherein said filtering the modulation spectrum comprises applying at least one of a bandpass filter, a bandstop filter, a highpass filter, and a lowpass filter to the modulation spectrum in order to at least reduce noise components contained in the modulation spectrum.

13. The method of claim 11, wherein said transforming the filtered modulation spectrum into a time domain signal comprises:
  applying a first inverse transform to the filtered modulation spectrum, thereby obtaining a filtered frequency domain representation; and
  applying a second inverse transform to the filtered frequency domain representation, thereby obtaining the filtered time domain biosignal.

14. A system for filtering noise in a biosignal, the system comprising:
  a modulation spectrum generator for receiving a time signal representative of a biological activity and determining a modulation spectrum for the time signal, the modulation spectrum representing a signal frequency as a function of a modulation frequency, the time signal comprising a biological activity component and a noise component;
  a filtering unit for filtering the modulation spectrum in order to remove at least partially the modulation frequencies corresponding to noise; and
  a transformation unit for transforming the filtered modulation spectrum into a time domain signal, thereby obtaining a filtered biosignal and outputting the filtered biosignal;
  wherein the modulation spectrum generator is adapted to:
    apply a first transform to the time signal in order to obtain a time frequency representation of the time signal; and
    apply a second transform across a time dimension of the time frequency representation in order to obtain the modulation spectrum.

15. The system of claim 14, wherein the filtering unit is adapted to apply at least one of a bandpass filter, a bandstop filter, a highpass filter, and a lowpass filter to the modulation spectrum in order to at least reduce noise components contained in the modulation spectrum.

16. The system of claim 14, wherein the transformation unit is adapted to:
  apply a first inverse transform to the filtered modulation spectrum in order to obtain a filtered frequency domain representation; and
  apply a second inverse transform to the filtered frequency domain representation in order to obtain the filtered biosignal.

* * * * *